(12) United States Patent
Goldman et al.

(10) Patent No.: US 9,709,553 B2
(45) Date of Patent: Jul. 18, 2017

(54) TREATING MYELIN DISEASES WITH OPTIMIZED CELL PREPARATIONS

(75) Inventors: Steven Goldman, Webster, NY (US); Fraser J. Sim, Buffalo, NY (US)

(73) Assignee: University of Rochester, Rochester, NY (US)

( * ) Notice: Subject to any disclaimer, the term of this patent is extended or adjusted under 35 U.S.C. 154(b) by 879 days.

(21) Appl. No.: 12/990,874

(22) PCT Filed: May 7, 2009

(86) PCT No.: PCT/US2009/043140
§ 371 (c)(1),
(2), (4) Date: Nov. 3, 2010

(87) PCT Pub. No.: WO2009/137674
PCT Pub. Date: Nov. 12, 2009

(65) Prior Publication Data
US 2011/0059055 A1    Mar. 10, 2011

Related U.S. Application Data

(60) Provisional application No. 61/051,557, filed on May 8, 2008.

(51) Int. Cl.
| A61K 35/30 | (2015.01) |
| G01N 33/50 | (2006.01) |
| C12N 5/079 | (2010.01) |
| C12N 5/0797 | (2010.01) |
| A61K 35/12 | (2015.01) |

(52) U.S. Cl.
CPC ....... *G01N 33/5058* (2013.01); *C12N 5/0622* (2013.01); *C12N 5/0623* (2013.01); *A61K 35/12* (2013.01)

(58) Field of Classification Search
CPC .......................... A61K 35/30; G01N 33/5058
See application file for complete search history.

(56) References Cited

U.S. PATENT DOCUMENTS

| | | |
|---|---|---|
| 3,753,357 A | 8/1973 | Schwartz |
| 4,199,022 A | 4/1980 | Senkan et al. |
| 4,559,298 A | 12/1985 | Fahy |
| 6,692,957 B2 | 2/2004 | Goldman et al. |
| 7,150,989 B2 | 12/2006 | Goldman et al. |
| 8,206,699 B2 | 6/2012 | Goldman et al. |
| 8,227,247 B2 | 7/2012 | Zhang et al. |
| 2004/0253719 A1 | 12/2004 | Goldman |
| 2012/0100113 A1 | 4/2012 | Tesar et al. |
| 2012/0207744 A1 | 8/2012 | Medlein et al. |
| 2013/0004467 A1 | 1/2013 | Goldman et al. |
| 2015/0352154 A1 | 12/2015 | Goldman et al. |

FOREIGN PATENT DOCUMENTS

| | | |
|---|---|---|
| WO | 03/070171 A2 | 8/2003 |
| WO | 03070171 A3 | 11/2003 |

OTHER PUBLICATIONS

Berry et al., Cytology and lineage of NG2-positive glia, Journal of Neurocytology, vol. 31, p. 457-467, 2002.*
Terada et al., The tetraspanin Protein CD9, is expressed by progenitor cells committed to oligodendrogenesis and is linked to B1 Integrin, CD81, and Tspan-2, vol. 40, p. 350-359, 2002.*
Scoulding et al., Oligodendrocyte progenitors are present in the normal adult human CNS and in the lesions of multiple sclerosis, Brain, vol. 121, p. 2221-2228, 1998.*
PE anti-human CD140a (PDGFRalpha) antibody http://www.biolegend.com/pe-anti-human-cd140a-pdgfralpha-antibody-3727.html.*
http://www.pierce-antibodies.com/PDGF-RA--CD140a-antibody-Polyclonal--PA532545.html.*
Armstrong et al., "Pre-oligodendrocytes from adult human CNS," J. Neurosci., 12(4):1538-1547 (1992).
Dennis et al.,"DAVID: Database for Annotation, Visualization, and Integrated Discovery," Genome Biol., 4(5):P3 (2003).
Gentleman et al., "Bioconductor: open software development for computational biology and bioinformatics," Genome Biol., 5(10):R80-R80.16 (2004).
Hall et al., "Spinal cord oligodendrocytes develop from ventrally derived progenitor cells that express PDGF alpha-receptors," Development, 122:4085-4094 (1996).
Irizarry et al., "Exploration, normalization, and summaries of high density oligonucleotide array probe level data," Biostatistics, 4(2):249-64 (2003).
Keyoung et al., "High-yield selection and extraction of two promoter-defined phenotypes of neural stem cells from the fetal human brain." Nature Biotechnology. 19:843-850 (2001).
Kirschenbaum et al., "In vitro neuronal production and differentiation by precursor cells derived from the adult human forebrain," Cerebral Cortex, 4(6):576-589 (1994).
LaRochelle et al., "Inhibition of platelet-derived growth factor autocrine growth stimulation by a monoclonal antibody to the human a platelet-derived growth factor receptor," Cell Growth Differ., 4(7):547-553 (1993).
Linner et al., "A new technique for removal of amorphous phase tissue water without ice crystal damage: a preparative method for ultrastructural analysis and immunoelectron microscopy," J. Histochem. Cytochem., 34 (9):1123-1135 (1986).
Matsui et al., "Independent expression of human α or β platelet-derived growth factor receptor cDNAs in a naïve hematopoietic cell leads to functional coupling with mitogenic and chemotactic signaling pathways," Proc. Natl. Acad. Sci. USA, 86:8314-8318 (1989).
Mazur, "The role of intracellular freezing in the death of cells cooled at supraoptimal rates," Cryobiology,14:251-272 (1977).

(Continued)

*Primary Examiner* — Taeyoon Kim
*Assistant Examiner* — Tiffany Gough
(74) *Attorney, Agent, or Firm* — LeClairRyan, a Professional Corporation

(57) ABSTRACT

The disclosure relates to oligodendrocyte-biased glial progenitor cells and methods of making, isolating, and using such cells.

12 Claims, 7 Drawing Sheets

(56) References Cited

OTHER PUBLICATIONS

Munson et al. "Ligand: a versatile computerized approach for characterization of ligand-binding systems," Anal. Biochem., 107:220-239 (1980).
Nunes et al., "Identification and isolation of multipotent neural progenitor cells from the subcortical white matter of the adult human brain," Nature Medicine, 9(4):439-447 (2003).
Pringle et al., "PDGF receptors in the rat CNS: during late neurogenesis, PDGF alpha-receptor expression appears to be restricted to glial cells of the oligodendrocyte lineage," Development, 115:535-551 (1992).
Rasband et al., "Developmental clustering of ion channels at and near the node of Ranvier," Dev. Biol., 236(1):5-16 (2001).
Readhead et al., "Expression of a myelin basic protein gene in transgenic shiverer mice: correction of the dysmyelinating phenotype," Cell, 48:703-712 (1990).
Roy et al., "Identification, isolation, and promoter-defined separation of mitotic oligodendrocyte progenitor cells from the adult human subcortical white matter," J. Neurosci., 19(22) 9986-9995 (1999).
Roy et al., "In vitro neurogenesis by progenitor cells isolated from the adult human hippocampus," Nature Med., 6:271-277 (2000).
Roy et al., "Telomerase-immortalization of neuronally restricted progentitor cells derived from the human fetal spinal cord," Nature Biotechnol., 22:297-305 (2004).
Schafer et al., "Glial regulation of the axonal membrane at nodes of Ranvier," Curr. Opinion in Neurobiology, 16:508-514 (2006).
Sherman et al., "Mechanisms of axon ensheathment and myelin growth," Nature Rev. Neurosci., 6:683-690 (2005).
Shinkai et al., "RAG-2 deficient mice lack mature lymphocytes owing to inability to initiate V(D)J rearrangement," Cell, 68(5): 855-67 (1992).
Sim et al., "Complementary patterns of gene expression by human oligodendrocyte progenitors and their environment predict determinants of progenitor maintenance and differentiation," Ann. Neurol., 59(5):763-79 (2006).
Smyth, "Linear models and empirical bayes methods for assessing differential expression in microarray experiments," Stat. Appl. Genet. Mol. Bio., 3:Article 3 (2004).
Takahashi et al., "Induction of pluripotent stem cells from mouse embryonic and adult fibroblast cultures by defined factors," Cell, 126(4):663-676 (2006).
Windrem et al., "Progenitor cells derived from the adult human subcortical white matter disperse and differentiate as oligodendrocytes within demyelinated lesions of the rat brain," J. Neurosci. Res., 69(6):966-75 (2002).
Windrem et al., "Neonatal chimerization with human glial progenitor cells can both remyelinate and rescue the otherwise lethally hypomyelinated shiverer mouse," Cell Stem Cell, 6:553-65 (2008).
Windrem et al., "Fetal and adult human oligodendrocyte progenitor cell isolates myelinate the congeniatally dysmyelinated brain," Nature Medicine, 10(1):93-97 (2004).
Yang et al., "βIV spectrin is recruited to axon initial segments and nodes of Ranvier by ankyrinG," J. Cell Biol., 176:509-519 (2007).
Yu et al. "Induced pluripotent stem cell lines derived from human somatic cells." Science, 318(5858):1917-20 (2007).
European Search Report for corresponding European Patent Application No. 09743660.4 (Dec. 11, 2011).
Communication for corresponding European Patent Application No. 09743660.4 (Mar. 27, 2014).
Chung et al., "Human Embryonic Stem Cell Lines Generated without Embryo Destruction," Cell Stem Cell 2(2):113-117 (2008).
Li et al., "Oligodendrocyte progenitor Cells in the Adult Rat CNS Express Myelin Oligodendrocyte Glycoprotein (MOG)," Brain Pathol. 12(4):463-471 (2002).
Crang et al., "The Demonstartion by Transplantation of the Very Restricted Remyelinating Potential of Post-Mitotic Oligodendrocytes," J. Neurocytol. 27(7):541-553 (1998).

Sim et al., "CD140a Identifies a Population of Highly Myelinogenic, Migration-Competent and Efficiently Engrafting Human Oligodendorcyte Progenitor Cells," Nat. Biotechnol. 29(10):934-941 (2011).
Office Action for corresponding Canadian Patent Application No. 2,723,382, 4 pages (May 27, 2015).
Written Opinion for corresponding International Application No. PCT/US2009/043140, 6 pages (mailed on Mar. 8, 2010).
Summons to Attend Oral Proceedings for corresponding European Patent Application No. 09743660.4, 5 pages (Sep. 28, 2015).
Sim et al., "Fate Determination of Adult Human Glial Progenitor Cells," Neuron Glia Biol. 5(3/4): 45-55 (2009).
UniProt, UniProtKB—P16234 (PDGFRA_Human), available at http://www.uniprot.org/uniprot/P16234, accessed Jan. 20, 2016.
Hu et al., "Neural Differentiation of Human Induced Pluripotent Stem Cells Follows Developmental Principles But With Variable Potency," Proc Natl Acad Sci USA 107(9):4335-40 (2010).
Hu et al., "Differentiation of Human Oligodendrocytes From Pluripotent Stem Cells," Nat Protoc. 4(11)1614-22 (2009).
Hu et al., "Human Oligodendrocytes From Embryonic Stem Cells: Conserved SHH Signaling Networks and Divergent FGF Effects," Development 136(9):1443-52 (2009).
Sullivan et al., "Induced Pluripotent Stem Cells: Epigenetic Memories and Practical Implications," Mol Hum Reprod 16(12):880-5 (2010).
Chin et al., "Induced Pluripotent Stem Cells and Embryonic Stem Cells are Distinguished by Gene Expression Signatures," Cell Stem Cell 5(1):111-23 (2009).
Abbaszadeh et al., "Bone Marrow Stromal Cell Transdifferentiation into Oligodendrocyte-Like Cells Using Triiodothyronine as a Inducer with Expression of Platelet-Derived Growth Factor Alpha as a Maturity Marker," Iranian Biomedical Journal 17(2):62-70 (2013).
Han et al., "Direct Reprogramming of Fibroblasts into Neural Stem Cells by Defined Factors," Cell Stem Cell 10:465-472 (2012).
Chua et al., "Neural Progenitors, Neurons and Oligodendrocytes from Human Umbilical Cord Blood Cells in a Serum-Free, Feeder-Free Cell Culture," Biochemical and Biophysical Research Communications 379:217-221 (2009).
Ben-Hur et al., "Prospects of Cell Therapy for Disorders of Myelin," Ann. N.Y. Acad. Sci. 1142:218-249 (2008).
Supplementary Search Report and Search Opinion for EP14749594.9 dated Jun. 20, 2016.
Goldman et al., "Glial Progenitor Cell-Based Treatment and Modeling of Neurological Disease," Science 338:491-495 (2012).
Pouya et al., "Human Induced Pluripotent Stem Cells Differentiation into Oligodendrocyte Progenitors and Transplantation in a Rat Model of Optic Chiasm Demyelination," PLos ONE 6(11):e27925 (2011).
Wang et al., "Human iPSC-Derived Oligodendrocyte Progenitor Cells Can Myelinate and Rescue a Mouse Model of Congenital Hypomyelination," Cell Stem Cell 12:252-264 (2013).
International Search Report and Written Opinion for International Application No. PCT/US14/15019 (mailed May 7, 2014).
International Preliminary Report on Patentability for International Application No. PCT/US14/15019 (issued Aug. 11, 2015).
International Preliminary Report on Patentability for International Application No. PCT/US2009/043140 (issued Nov. 9, 2010).
International Search Report for International Application No. PCT/US2009/043140 (mailed on Mar. 8, 2010).
Office Action in U.S. Appl. No. 14/764,507 (dated Dec. 22, 2016).
Abeyta et al., "Unique Gene Expression Signature of Independently-Derived Human Embryonic Stem Cell Lines," Human Molecular Genetics 13(6):601-8 (2004).
Allegrucci et al., "Differences Between Human Embryonic Stem Cell Lines," Human Reproduction Update, Advanced Access published on Aug. 26, 2006, pp. 1-18.
Bellin et al., "Induced Pluripotent Stem Cells: The new Patient?," Nature Reviews Molecular Cell Biology 13:713-26 (2012).
Burridge et al., "A Universal System for Highly Efficient Cardiac Differentiation of Human Induced Pluripotent Stem Cells That Eliminates Interline Variability," PLoS ONE 6(4):e18293, 1-16 (2011).

(56) References Cited

OTHER PUBLICATIONS

Narsinh et al., "Comparison of Human Induced Pluripotent and Embryonic Stem Cells: Fraternal or Identical Twins?," Molecular Therapy 19(4):635-8 (2011).
Rao et al., "Conserved and Divergent Paths that Regulate Self-Renewal in Mouse and Human Embryonic Stem Cells," Developmental Biology 275:269-86 (2004).

* cited by examiner

TREATING MYELIN DISEASES WITH OPTIMIZED CELL PREPARATIONS

CROSS REFERENCE TO RELATED APPLICATIONS

This application claims the benefit of U.S. Provisional Application No. 61/051,557, filed May 8, 2008, which is incorporated by reference in its entirety as part of this application.

STATEMENT REGARDING FEDERALLY SPONSORED RESEARCH

This invention was made with government support under Grant No. R01NS039559 awarded by the National Institute of Neurological Disorders and Stroke. The government has certain rights in the invention.

BACKGROUND

Myelin failure or loss characterizes acquired and congenital myelin diseases. These hypomyelination disorders and demyelinating disorders have profound clinical effects and, in many cases, result in severe disabilities or reduced life spans in patients with the disorders. Few treatment options are currently available to these patients.

SUMMARY

This disclosure relates to oligodendrocyte-biased glial progenitor cells and methods of making, isolating, and using such cells. Provided herein is a method of isolating a population of oligodendrocyte-biased glial progenitor cells that includes the steps of providing a population of neural cells or neural precursor cells and selecting for the presence of a PDGFαR marker and/or a CD9 marker on the neural cells or neural precursor cells to isolate oligodendrocyte-biased glial progenitor cells.

Also provided is a method of isolating a population of oligodendrocyte-biased glial progenitor cells comprising the steps of providing a population of neural cells or neural precursor cells, selecting for the presence of A2B5 on the neural cells or neural precursor cells, selecting for the absence of PSA-NCAM or other marker for neuronal cell lineage on the neural cells or neural precursor cells, and selecting for the absence of CD11 or other marker for inflammatory cells (like cells of microglial lineage) on the neural cells or neural precursor cells, thus, isolating a population of A2B5 positive, PSA-NCAM negative, CD11 negative oligodendrocytes-biased glial progenitor cells.

A substantially pure population of oligodendrocyte-biased glial progenitor cells is provided. The cells are positive for a PDGFαR marker and/or a CD9 marker and are optionally immortalized. By way of example, cells of the population of oligodendrocyte-biased glial progenitor cells express an exogenous nucleic acid encoding a human telomeric extension reverse transcriptase.

Also provided is a population of cells comprising at least about 80% oligodendrocyte-biased glial progenitor cells. The oligodendrocyte-biased glial progenitor cells are optionally positive for a CD9 marker, for a PDGFαR marker, or for both a CD9 marker and a PDGFαR marker. In an example population the glial progenitor cells are positive for a CD9 marker and the CD9 positive cells are optionally negative for a PDGFαR marker. In an example population the glial progenitor cells are positive for a PDGFαR marker and are positive for a CD9 marker. In an example population, the glial progenitor cells are positive for a PDGFαR marker and negative for a CD9 marker. Further provided is a population of glial progenitor cells, wherein at least about 80% of the glial progenitor cells are positive for a PDGFαR marker, a CD9 marker, or for both markers.

Also provided are methods of treating a subject having a myelin-related disorder (e.g., a hypomyelination disorder, such has leukodystrophy, lysosomal storage disease, cerebral palsy, or periventricular leukomalacia, or a demyelinating disorder such as an inflammatory or inherited demyelinating disorder). The methods of treatment include transplanting into the subject a population of oligodendrocyte-biased glial progenitor cells taught herein or made by a method taught herein.

Methods of making an oligodendrocyte-biased glial progenitor cell line are also provided. The methods include the steps of isolating a population of neural cells or neural precursor cells, selecting for the presence of PDGFαR and or CD9 on the neural cells or neural precursor cells, and immortalizing the cells to make an oligodendrocyte-biased glial progenitor cell line.

The cells and methods of making or isolating the oligodendrocyte-biased glial progenitor cells taught herein are useful in methods of screening for agents that modulate glial progenitor cell fate. Thus, provided herein are methods of screening for agents that modulate glial progenitor cell fate, which include culturing a population of oligodendrocyte-biased glial progenitor cells taught herein or a population of oligodendrocyte-biased glial progenitor cells made by a method taught herein. The cultured cells are contacted with an agent to be screened and the fate of the cells contacted with the agent is detected. An increase or decrease in oligodendrocyte fate or an increase or decrease in astrocyte fate indicates an agent that modulates glial cell fate.

The details of one or more methods or compositions are set forth in the accompanying drawings and the description below. Other features, objects, and advantages of the methods and compositions will be apparent from the description and drawings, and from the claims.

DESCRIPTION OF DRAWINGS

FIG. 4A shows the relative fractions six sub-fractions calculated from the a combined MACS and FACS procedure (n=4, 19-22 wk gestational age). Each sort was then plated in T3/0.5% pd-FBS containing media for 7 days then stained and counted for the oligodendrocyte antigen O4 (FIG. 4B). Each CD140a$^+$ fraction regardless of A2B5 or PSA-NCAM status gave rise to a higher proportion of O4$^+$ oligodendrocytes (n=3 samples).

FIG. 5A shows the proportion of O4-expressing immature oligodendrocytes was counted at 4 days in vitro. Almost no oligodendrocytes were found in CD140a-depleted cultures, in contrast approximately 40% of all CD140a$^+$ cells had developed as oligodendrocytes.

DETAILED DESCRIPTION

Figure 1:
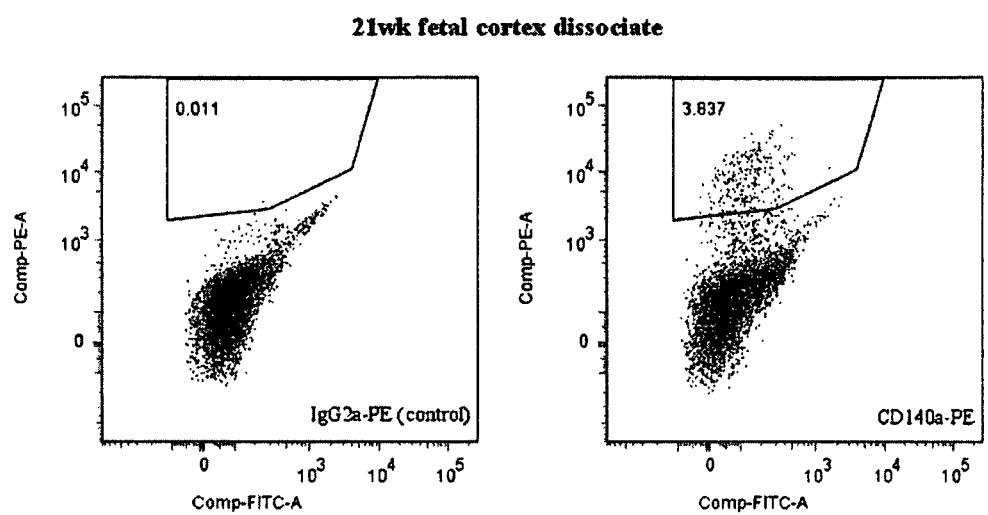
FIG. 1 is a flow cytometry analysis for CD140a/PDGFαR using dissociated fetal human (21 week gestational age) cortical tissue. Mouse anti-human CD140a antibody recognized a discrete population of cells in the fetal human cortex.

Neural cells and neural precursor cells from both adult and fetal sources include diverse populations of cells, including cells of neuronal linage and glial cell lineage. It has proven challenging to isolate relatively pure populations of specific cell types from mixed populations of cells. This has proven even more difficult when high yields of a particular cell type are desired for cellular transplants.

For example, A2B5 has been used as an early marker for, and means of isolation of, glial progenitor cells. A2B5 recognizes epitopes on several gangliosides that are synthesized by GD3 synthase. However, the GD3 synthase enzyme is active in bipotential oligodendrocyte-astrocyte progenitors, immature neuroblasts and in mature fibrous astrocytes. Thus, a second step is used to identify and eliminate neuronal cells. By double sorting to deplete A2B5-sorted cells of PSA-NCAM$^+$ (polysialylated neural cell adhesion molecule-positive) neuroblasts, populations of neural cells are enriched for glial cell precursors. These steps, however, do not eliminate fibrous astrocytes, which remain an abundant contaminant when relatively pure populations of oligodendrocyte precursors cells are needed. As oligodendrocytes are the myelinating cells of the central nervous system, relatively pure populations of oligodendrocyte precursors are useful for transplantation in subjects with myelin diseases.

Cell Populations, Compositions, and Kits

Provided herein are populations of oligodendrocyte-biased glial progenitor cells. Oligodendrocyte-biased glial progenitor cells can optionally give rise to both oligodendrocytes and astrocytes. The described cell populations therefore include populations of bipotential oligodendrocyte biased glial progenitor cells.

An example population comprises at least about 80% oligodendrocyte-biased glial progenitor cells, including, for example, about 80%, 85%, 90%, 95%, 96%, 97%, 98%, 99%, 100% oligodendrocyte-biased glial progenitor cells. The oligodendrocyte-biased glial progenitor cells are optionally positive for a CD9 marker, for a PDGFαR marker, or for both a CD9 marker and a PDGFαR marker. In an example population the glial progenitor cells are positive for a CD9 marker and the CD9 positive cells are optionally negative for a PDGFαR marker. In an example population the glial progenitor cells are positive for a PDGFαR marker and are positive for a CD9 marker. In an example population, the glial progenitor cells are positive for a PDGFαR marker and negative for a CD9 marker. Further provided is a population of glial progenitor cells, wherein at least about 80% of the glial progenitor cells are positive for a PDGFαR marker, a CD9 marker, or for both markers.

The cell populations can be relatively devoid (e.g., containing less than 20, 15, 10, 9, 8, 7, 6, 5, 4, 3, 2, or 1%) of other cells types such as neurons or cells of neuronal lineage, fibrous astrocytes and cells of fibrous astrocyte lineage, and pluripotential stem cells (like ES cells). Optionally, example cell populations are substantially pure populations of oligodendrocyte-biased glial progenitor cells.

The oligodendrocyte-biased glial progenitor cells of a described population can be positive for a PDGFαR marker. The PDGF marker is optionally a PDGFαR ectodomain. One example PDGFαR ectodomain epitope that can be used to indicate and/or select one or more PDGFαR positive cells is CD140a. Thus, PDGFαR positive cells can be identified by CD140a and a population of PDGFαR positive cells can be enriched using CD140a. Such cells can be referred to as PDGFαR$^+$/CD140a$^+$.

By positive for a PDGFαR marker is meant that PDGFαR-specific antibodies or other specific binding entities like PDGFα selectively bind to the marker, such that PDGFαR antibodies or other binding moieties can be used in cell isolation and enriching procedures, like immunopanning. PDGFαR is expressed by glial progenitor cells and by more restricted oligodendrocyte progenitors but is sharply down-regulated in mature astrocytes. According to human and rodent gene expression analyses, PDGFαR is selectively overexpressed in A2B5-defined progenitors.

Oligodendrocyte-biased glial progenitor cell populations can be positive for a CD9 marker. The CD9 marker is optionally a CD9 ectodomain. By positive for a CD9 marker is meant that CD9-specific antibodies selectively bind to the CD9 marker, such that CD9 antibodies or other binding moieties can be used in cell isolation or enrichment procedures, like immunopanning. Cells positive for CD9 can also be positive for PDGFαR. Optionally, cells positive for PDGFαR are negative for CD9. Optionally, cells positive for CD9 are negative for PDGFαR.

Optionally, the oligodendrocyte-biased glial progenitor cells of a described population are negative for a PSA-NCAM marker and/or other markers for cells of neuronal lineage, negative for one or more inflammatory cell markers (e.g., negative for a CD11 marker, negative for a CD32 marker, and/or negative for a CD36 marker), which are markers for microglia. Optionally, the oligodendrocyte-biased glial progenitor cells of a population are negative for any combination or subset of these additional markers. Thus, for example, the oligodendrocyte-biased glial progenitor cells of a population can be negative for any one, two, three, or four of these additional markers.

The oligodendrocyte-biased glial progenitor cells of a population can be positive or negative for an A2B5 marker. Thus, a population can be further selected based on either the presence or absence of the A2B5 marker. Thus, the oligodendrocyte-biased glial progenitor cells of a population can be A2B5 positive, A2B5 negative or a combination of A2B5 positive and negative cells. The A2B5 negative cells in a population can further be negative for a PSA-NCAM marker, a CD11 marker, a CD32 marker, a CD36 marker, or any combination. Similarly, the A2B5 positive cells can further be negative for a PSA-NCAM marker, a CD11 marker, a CD32 marker, a CD36 marker, or any combination.

Optionally, the described populations of oligodendrocyte-biased glial progenitor cells can be derived from neural tissue or from either pluripotent or multipotent stem cells or cell lines. The pluripotent stem cells can be induced pluripotent stem cells (IPS cells). IPS cells are derived, for example, from differentiated cells like fibroblasts. (See, Yu, 2007, Science 21; 318(5858):1917-20 and Takahashi, 2006, Cell, 126; 4, 663-676, which are both incorporated by reference in their entirety for the methods and compositions described therein). Optionally, the oligodendroctye biased glial progenitor cells are derived from fetal cells. However, the cells can be derived from non-fetal tissue, including for example, adult neural tissue or non-neural tissue (e.g., in the case of an IPS cell). The neural tissue optionally is derived from the brain, brainstem or spinal cord, including the subventricular zone, olfactory bulb, subcortical white matter, and cerebrum of both the fetal and adult brain, and also the ganglionic eminences of the fetal brain.

A selected population of the oligodendrocyte-biased glial progenitor cells can be optionally cultured under conditions that cause differentiation of oligodendrocytes. A population of the oligodendrocyte-biased glial progenitor cells can be optionally cultured under conditions that cause differentiation of astrocytes. Thus the fate of oligodendrocyte-biased glial progenitor cells of a oligodendrocyte-biased glial progenitor cell population can be directed to form oligodendroctye or astroctyes. For example, in vitro oligodendroctye differentiation can be promoted from PDGFαR marker positive cells by T3 and mitogen removal in serum-free media. In vitro astrocyte differentiation can be promoted from PDGFαR marker positive cells by serum and/or BMP exposure.

The described populations of oligodendrocyte-biased glial progenitor cells can be optionally expanded in culture to increase the total number of cells. The cells can be expanded by either continuous or pulsatile exposure to PDGF-AA or AB as mitogens that support the expansion of oligodendrocyte-biased glial progenitor cells; they can be exposed to fibroblast growth factors, including FGF2, FGF4, FGF8 and FGF9, which can support the mitotic expansion of the glial progenitor cells, but which can bias their differentiation to a mixed population of astrocytes as well as oligodendrocytes. They can also be expanded in media supplemented with combinations of FGF2, PDGF, and NT3, which can optionally be supplemented with either platelet-depleted or whole serum (see Nunes et al. (2003), Identification and isolation of multipotent neural progenitor cells from the subcortical white matter of the adult human brain. Nature Medicine 9:239-247; Windrem et al. (2004), Fetal and adult human oligodendrocyte progenitor cell isolates myelinate the congenitally dysmyelinated brain. Nature Medicine 10:93-97, which are incorporated by reference for the methods and compositions described therein).

Furthermore, the populations of oligodendrocyte-biased glial progenitor cells can be optionally immortalized Immortalized cells include cell lines that divide repeatedly in culture Immortalized cells are optionally developed by genetic modification of a parent cell. By way of example, a population of cells that includes oligodendrocyte-biased glial progenitor cells can be transduced to express an exogenous nucleic acid encoding a human telomeric extension reverse transcriptase (hTERT) (see Roy et al. (2004), Telomerase-immortalization of the human fetal spinal cord ventricular zone generates stable lines of lineage-restricted spinal progenitor cells, Nature Biotechnol. 22:297-305; also U.S. Pat. No. 7,150,989, entitled "Telomerase-immortalized human neural stem cells and phenotypically-restricted progenitor cells," to Goldman, which are incorporated by reference in their entireties for the methods and compositions described therein). The human telomeric extension reverse transcriptase is optionally operably linked to a promoter, that directs the expression of hTERT in the cells. The promoter can be expressed constitutively, meaning in both the transduced progenitor cells and the progeny, or in a cell-specific fashion, meaning in a subset of the derivatives of the initially transduced cell population.

The populations of oligodendrocyte-biased glial progenitor cells are optionally genetically modified to express other proteins of interest. For example, the cell can be modified to express an exogenous targeting moiety, an exogenous marker (for example, for imaging purposes), or the like. The oligodendrocyte-biased glial progenitor cells of the populations can be optionally modified to overexpress an endogenous targeting moiety, marker, or a myelin basic protein or the like.

Optionally the cell populations are cryopreserved. Various methods for cryopreservation of viable cells are known and can be used (see, e.g., Mazur, 1977, Cyrobiology 14:251-272; Livesey and Linner, 1987, Nature 327:255; Linner, et al., 1986, J. Histochem. Cytochem. 34(9):1123-1135; U.S. Pat. No. 4,199,022 to Senkan et al.; U.S. Pat. No. 3,753,357 to Schwartz; U.S. Pat. No. 4,559,298 to Fahy, which are incorporated by reference at least for the methods and compositions described therein).

Provided herein is a pharmaceutical composition comprising an effective amount of the oligodendrocyte-biased glial progenitor cell population and a pharmaceutically acceptable carrier. Pharmaceutically acceptable carriers are described below.

Also provided herein are kits that include reagents that can be used in practicing the methods disclosed herein and kits comprising the cell populations taught herein. The kits can include any reagent or combination of reagents that would be understood to be required or beneficial in the practice of the disclosed methods. For example, the kits can include cell populations, as well as the buffers or compositions required to use them. Other examples of kits, include reagents for cell sorting and or detection, optionally with buffers or compositions required to use them. The kits can also include oligodendrocyte-biased precursor cells and instructions to use the same in the methods described herein.

Also provided herein are populations of oligodendrocyte-biased glial progenitor cells made or isolated by the methods taught herein.

Methods of Making or Isolating a Population of Oligodendrocyte-biased Glial Progenitor Cells The methods disclosed herein to isolate populations of oligodendrocyte-biased glial progenitor cells relate to selecting for the presence of a PDGFαR marker or to select for the presence of A2B5, along with the absence of PSA-NCAM and CD11. The methods disclosed herein to isolate populations of oligodendrocyte-biased glial progenitor cells can also relate to selecting for the presence of a CD9 marker. Optionally, the methods include selecting for the presence of a CD9 marker and/or a PDGFαR marker. The methods are designed to provide a higher yield and/or further enrichment of a particular cell type (i.e., oligodendrocyte-biased glial progenitor cells). The methods optionally include selecting for or against other markers.

Thus, provided herein are methods of isolating a population of oligodendrocyte-biased glial progenitor cells that include the steps of providing a population of neural cells or neural precursor cells and selecting for the presence of a PDGFαR marker on the neural cells or neural precursor cells to isolate oligodendrocyte-biased glial progenitor cells.

Also provided herein are methods of isolating a population of oligodendrocyte-biased glial progenitor cells that include the steps of providing a population of neural cells or neural precursor cells and selecting for the presence of a CD9 marker on the neural cells or neural precursor cells to isolate oligodendrocyte-biased glial progenitor cells.

The methods optionally further include selecting for either the presence or absence of additional markers. Thus, the methods optionally include selecting for the presence or absence of A2B5 on the neural cells or neural precursor cells. The methods optionally further include selecting for the absence of PSA-NCAM, the absence of CD11, the absence of CD32, or the absence of CD36.

Another method of isolating a population of oligodendrocyte-biased glial progenitor cells includes the steps of providing a population of neural cells or neural precursor cells, and performing several selection steps including selecting for the presence of A2B5 on the neural cells or neural precursor cells, selecting for the absence of PSA-NCAM on the neural cells or neural precursor cells, selecting for the absence of CD11 on the neural cells or neural precursor cells to isolate a population of A2B5 positive, PSA-NCAM negative, CD11 negative oligodendrocytes-biased glial progenitor cells. The method optionally further includes selecting for the absence of CD32, CD36, or both CD32 and CD36. This method results in a different population of oligodendrocyte-biased glial progenitor cells as compared to the single step method using the PDGFαR marker, because certain of the PDGFαR+ cells are A2B5- and some are positive. This multistep method results in an A2B5+ subpopulation.

As described above, the neural cells or neural precursor cells used in the method are optionally derived from neural tissue, differentiated stem cells, stem cells, or cell lines. Methods of acquiring neural cells or tissue and/or neural precursor cells and tissue are known in the art. By way of example, neural tissue can be acquired by biopsy. The source of the tissue or cells can be any mammalian source, including a human; a domesticated animal, such as cats and dogs; livestock (e.g., cattle, horses, pigs, sheep, and goats); laboratory animals (e.g., mice, rabbits, rats, and guinea pigs); non-human primates.

The selection steps taught herein can be performed concurrently or serially in any order. Selection for a particular marker, such as a PDGFαR marker and/or a CD9 marker, can be performed using conventional methods such as immunopanning. The selection methods optionally involve the use of fluorescence sorting (FACS), magnetic sorting (MACS) or any other methods that allow a rapid, efficient cell sorting. Examples of methods for cell sorting are taught for example in U.S. Pat. No. 6,692,957, which is incorporated by reference herein in its entirety, at least for compositions and methods for cell selection and sorting.

Generally, cell sorting methods can use a detectable moiety. Detectable moieties include any suitable direct or indirect label, including, but not limited to, enzymes, fluorophores, biotin, chromophores, radioisotopes, colored beads, electrochemical, chemical-modifying or chemiluminescent moieties. Common fluorescent moieties include fluorescein, cyanine dyes, coumarins, phycoerythrin, phycobiliproteins, dansyl chloride, Texas Red, and lanthanide complexes or derivatives thereof. Magnetic cell sorting may be used.

When cell sorting is performed, the marker can be an ectodomain and cell permeabilization or membrane disruption are not used. By way of example, the PDGFαR marker selection step is optionally performed using an antibody or other binding moiety that binds an ectodomain of the PDGFαR (e.g. CD140a). Suitable antibodies include, but are not limited to, monoclonal and polyclonal antibodies, chimeric antibodies, antibody fragments (e.g., F(ab')2, Fab', Fab fragments) capable of binding the selected marker, and single chain antibodies. Other binding moieties include marker ligands, cofactors, and the like that specifically bind to the marker. Thus, in the case of a marker that is a receptor, a receptor ligand or binding portion thereof can be used as a detectable moiety. Antibodies and other binding moieties are commercially available or can be made using techniques available to a skilled artisan.

One of skill in the art will understand how to select for or against a specific marker. Thus, by way of example, a population of cells sorted for a particular marker includes identifying cells that are positive for that particular marker and retaining those cells for further use or further selection steps. A population of cells sorted against a specific marker includes identifying cells that are positive for that particular marker and excluding those cells for further use or further selection steps.

Optionally, the methods of isolation further comprise immortalizing the cells. Immortalized cells include cell lines that can divide in culture following repeated passaging Immortalized cells are optionally developed by genetic modification of a parent cell. By way of example, the methods of isolation further comprise modifying the neural cells, neural precursor cells, or any subpopulation thereof that includes oligodendrocyte-biased glial progenitor cells so that the cells express an exogenous nucleic acid encoding a human telomeric extension reverse transcriptase. Materials and methods for immortalizing progenitor cells using telomeric extension reverse transcriptase are disclosed in U.S. Pat. No. 7,150,989, which is incorporated herein by reference in its entirety at least for the teachings related to telomerase immortalization Immortalization can be performed prior to or after one or more of the selection steps of the methods.

Thus provided herein is a method of making an oligodendrocyte-biased glial progenitor cell line including the steps of providing a population of neural cells or a population of oligodendrocyte-biased glial progenitor cells made by the methods taught herein and immortalizing the cells to produce a cell line. The immortalization step optionally comprises introducing into the cells a nucleic acid sequence encoding human telomeric extension reverse transcriptase operably linked to a promoter. Introduction of the exogenous nucleic acid can be accomplished by various means including by viral-mediated transduction, electroporation, biolistic transduction, or liposomal-mediated transduction. Viral-mediated transduction means can be selected from the group consisting of retrovirus-mediated transduction, adeno-associated virus-mediated transduction, lentivirus-mediated transduction, adenovirus-mediated transduction, and herpesvirus-mediated transduction.

Methods of Treatment

Provided herein are methods of treating a myelin-related disorder in a subject. The methods can include the step of transplanting into the subject a population of oligodendrocyte-biased glial progenitor cells made by the methods taught herein or using a population of oligodendrocyte-biased glial progenitor cells taught herein. The methods can also include culturing a selected population of oligodendrocyte-biased glial progenitor cells under conditions that cause differentiation of the oligodendrocytes. The resulting differentiated oligodendrocytes, or a subset thereof, can then be transplanted into the subject having a myelin-related disorder.

Myelin-related disorders include hypomyelination disorders and demyelinating disorders. Hypomyelination disorders include leukodystrophy, a lysosomal storage disease, cerebral palsy, and periventricular leukomalacia. Demyelinating disorders include inflammatory demyelinating disorders such as multiple sclerosis, transverse myelitis, and optic neuritis and inherited demyelinating disorders.

Autologous, allogeneic or xenogeneic cells can be used in the transplantation step. The neural cells or neural precursor cells, and/or the glial progenitor cells derived therefrom, can be derived from various sources as described above. Autologous neural cells or neural precursor cells can be harvested, for example, from the subventricular zone of the transplant recipient. Allogeneic cells can be harvested from aborted embryos, unused fertility derived embryos, or from organ donors. Xenogeneic cells can be harvested from a pig, monkey, or any other suitable mammal. As discussed above, the transplanted cells are optionally immortalized. Cell lines of stem cells and differentiated cells can be used to derive the glial progenitor cells to avoid the use of embryonic tissue and/or neural tissue.

Since the CNS is a immunologically privileged site, transplanted cells, including xenogeneic, can survive and, optionally, no immunosuppressant drugs or a typical regimen of immunosuppressant agents are used in the treatment methods. The methods of treatment, however, optionally further comprise administering an immunosuppressant agent to the subject Immunosuppressant agents and their dosing regimens are known to one of skill in the art and include such agents as Azathioprine, Azathioprine Sodium, Cyclosporine, Daltroban, Gusperimus Trihydrochloride, Sirolimus, and Tacrolimus. Dosages ranges and duration of the regimen can be varied with the disorder being treated; the extent of rejection; the activity of the specific immunosuppressant employed; the age, body weight, general health, sex and diet of the subject; the time of administration; the route of administration; the rate of excretion of the specific immunosuppressant employed; the duration and frequency of the treatment; and drugs used in combination. One of skill in the art can determine acceptable dosages for and duration of immunosuppression. The dosage regimen can be adjusted by the individual physician in the event of any contraindications or change in the subject's status.

The number of oligodendrocyte-biased progenitor cells or oligodendrocytes transplanted can range from about $10^2$-$10^8$ at each transplantation (e.g., injection site), depending on the size and species of the recipient, and the volume of tissue requiring myelin production or replacement. Single transplantation (e.g., injection) doses can span ranges of $10^3$-$10^5$, $10^4$-$10^7$, and $10^5$-$10^8$ cells, or any amount in total for a transplant recipient patient.

Delivery of the cells to the subject can include either a single step or a multiple step injection directly into the nervous system. For localized disorders such as demyelination of the optic nerve, a single injection can be used. Although adult and fetal oligodendrocyte precursor cells disperse widely within a transplant recipient's brain (Windrem et al., Nature Medicine 10: 93-97), for widespread demyelinating or hypomyelination disorders, multiple injections sites can be performed to optimize treatment. Injection is optionally directed into areas of the central nervous system such as white matter tracts like the corpus callosum (e.g., into the anterior and posterior anlagen), dorsal columns, cerebellar peduncles, cerebral peduncles. Such injections can be made unilaterally or bilaterally using precise localization methods such as stereotaxic surgery, optionally with accompanying imaging methods (e.g., high resolution MRI imaging). One of skill in the art recognizes that brain regions vary across species; however, one of skill in the art also recognizes comparable brain regions across mammalian species.

The cellular transplants are optionally injected as dissociated cells but can also be provided by local placement of non-dissociated cells. In either case, the cellular transplants optionally comprise an acceptable solution. Such acceptable solutions include solutions that avoid undesirable biological activities and contamination. Suitable solutions include an appropriate amount of a pharmaceutically-acceptable salt to render the formulation isotonic. Examples of the pharmaceutically-acceptable solutions include, but are not limited to, saline, Ringer's solution, dextrose solution, and culture media. The pH of the solution is preferably from about 5 to about 8, and more preferably from about 7 to about 7.5.

The injection of the dissociated cellular transplant can be a streaming injection made across the entry path, the exit path, or both the entry and exit paths of the injection device (e.g., a cannula, a needle, or a tube). Automation can be used to provide a uniform entry and exit speed and an injection speed and volume.

Optionally a multifocal delivery strategy can be used, for example as described in the examples. Such a multifocal delivery strategy is designed to achieve widespread and dense donor cell engraftment throughout the recipient central nervous system. Injection sites can be chosen to permit contiguous infiltration of migrating donor cells into major brain areas, brainstem, and spinal while matter tracts, without hindrance (or with limited hindrance) from intervening gray matter structures. For example, injection sites optionally include four locations in the forebrain subcortex, specifically into the anterior and posterior anlagen of the corpus callosum bilaterally, and into a fifth location in the cerebellar peduncle dorsally.

Optionally, the methods of treatment provided herein further comprise assessing remyelination directly or indirectly. For example, imagining technique, conduction velocities, or symptomatic improvement are optionally tested subsequent to engraftment.

Methods of Screening

Also provided herein are methods of screening for agents that modulate glial progenitor cell fate using the cell populations taught herein or cells made by the methods taught herein. The method can include the steps of culturing the population of oligodendrocyte-biased glial progenitor cells; contacting the cultured cells with an agent to be screened; and detecting the fate of cells contacted with the agent. An increase or decrease in oligodendrocyte fate or an increase or decrease in astrocyte fate indicates an agent that modulates glial cell fate. Agents identified by such methods are useful, for example, in selecting an agent that increases the number of oligodendrocytes in vivo or in vitro. These agents are used to treat myelination disorders in a subject or are used to enrich grafts prior to transplantation. Conversely, an agent that reduces astrocyte fate can be used, for example, to reduce glial scarring or inflammatory reactions following injury of the nervous system in a subject.

The screening methods optionally include assessing the viability of the cells having a modulated glial cell fate. The viability and detection steps taught herein include detecting one or more oligodendrocyte or astrocyte specific markers. Such detection methods are known by the skilled artisan and include various procedures such as FACS and immunohistochemistry.

Additional Definitions

As used herein, the phrase specific binding or selective binding refers to a binding reaction which is determinative of the presence of the marker, such as PDGFαR, in a heterogeneous population of proteins, proteoglycans, and other biologics. Thus, under designated conditions, the antibodies or fragments thereof of the present invention bind to a particular marker or marker fragment or variant thereof without binding in a significant amount to other proteins, proteoglycans, or other biologics present in the subject.

Selective binding to an antibody can use an antibody that is selected for its specificity for a particular protein, proteoglycan, or variant, fragment, or protein core thereof. A variety of immunoassay formats may be used to select antibodies that selectively bind with a particular protein, proteoglycan, or variant, fragment, or protein core thereof. For example, solid-phase ELISA immunoassays are routinely used to select antibodies selectively immunoreactive with a protein, proteoglycan, or variant, fragment, or protein core thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem. 107:220 (1980).

Neural cells and neural precursor cells can include a combination of cells found in the nervous system or of cells that develop or can develop into neural tissue. For example, neural cells or neural precursor cells include cells derived from a fetal or non-fetal brain or spinal cord. Such neural cells or neural precursor cells can be a dissociated population of cells including neurons, stem cells, glial cells, or cells of neuronal or glial lineage. Neural cells are optionally derived from differentiated, non-neural cells, e.g, fibroblasts, using techniques used in the art.

By a substantially pure population of cells is meant that the cells having a selected phenotype (e.g., glial progenitor cells) constitute at least about 95% of the cell population. By at least about 95%, includes 95, 96, 97, 98, 99, or 100% of the cell population.

When values are expressed as approximations, by use of the antecedent about, the particular value is disclosed as well. The endpoints of each of the ranges are significant both in relation to the other endpoint, and independently of the other endpoint. Furthermore, where specific values are explicitly disclosed herein, that value, as well as about that value, are disclosed even if not explicitly stated. For example, if the value 10 is explicitly disclosed, then about 10 is also disclosed. When a value is explicitly disclosed, less than or equal to the value, greater than or equal to the value and possible ranges between values are also disclosed. For example, if the value 10 is disclosed then less than or equal to 10, as well as greater than or equal to 10 is also disclosed. It is also understood that, throughout the application, data are provided in a number of different formats, and these data represent endpoints and starting points, and ranges for any combination of the data points. For example, if a particular data point 10 and a particular data point 15 are disclosed, it is understood that greater than, greater than or equal to, less than, less than or equal to, and equal to 10 and 15 are considered disclosed as well as any the range between 10 and 15.

Optional or optionally, as used throughout, means that the subsequently described event or circumstance can, but may not occur, and that the description includes instances where said event or circumstance occurs and instances where it does not.

As used herein, a detectable moiety is any means for detecting an interaction between a marker and its binding moiety, thereby identifying the presence of the marker. The detectable moiety may be detected using various means of detection. The detection of the detectable moiety can be direct provided that the detectable moiety is itself detectable, such as, for example, in the case of fluorophores. Alternatively, the detection of the detectable moiety can be indirect. In the latter case, a second or third moiety reacts or binds with the detectable moiety. For example, an antibody that binds the marker can serve as an indirect detectable moiety to which a second antibody having a direct detectable moiety specifically binds.

As used herein treating or treatment does not necessarily mean a complete cure. It can also mean that one or more symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease or physiological state of the disease.

Disclosed are materials, compositions, and components that can be used for, can be used in conjunction with, can be used in preparation of, or are products of the disclosed method and compositions. These and other materials are disclosed herein, and it is understood that when combinations, subsets, interactions, groups, etc. of these materials are disclosed that, while specific reference of each various individual and collective combinations and permutation of these compounds may not be explicitly disclosed, each is specifically contemplated and described herein. For example, if a particular modification of a cell population or a treatment regimen is disclosed and discussed and a number of modifications that can be made to the cell population or regimen are discussed, each and every combination and permutation of the cell population and the regimen are specifically contemplated unless specifically indicated to the contrary. Likewise, any subset or combination of these is also specifically contemplated and disclosed.

EXAMPLES

Example 1

Identification of PDGFαR as a Marker for Oligodendrocyte-biased Precursor Cells A single marker was identified to avoid multistep isolation processes previously necessary to isolate oligodendrocyte-biased precursor cells. First, fetal human subcortical/cortical dissociates, derived from 18-21 week gestational age aborted fetuses, were tagged with anti-CD140a, an epitope of the PDGFαR protein. FACS of these dissociates recovered an average of 3.5% of the sorted cells as CD140a (FIG. 1). Multiplexed quantitative PCR using GeneCard® microfluidic arrays (Applied Biosystems, Foster City, Calif.) confirmed that these cells highly over-expressed markers of both bipotential glial and oligodendrocyte progenitor cells and were depleted in neuronal, astrocytic, and stem cell genes.

When cultured, these cells gave rise to oligodendrocytes or astrocytes, depending upon the culture conditions and growth factor complements to which they were exposed. Strikingly though, essentially all oligodendrocytes generated from these dissociates were derived from the PDGFαR-sorted pool. Matched preparations depleted of PDGFαR+ cells failed to generate appreciable numbers of O4-defined oligodendroglia under any conditions. The absolute enrichment in O4+ oligodendroglia afforded by antecedent PDGFαR-based MACS was at least 15-fold, and the few oligodendrocytes noted in the PDGFαR-depleted cultures were within the false negative incidence of PDGFαR+ cells that might have been expected to escape into the nominally MACS depleted fraction. Two-color FACS then revealed that, whereas A2B5+PDGFαR− cells were almost 6-times as abundant as A2B5+PDGFαR+ cells, essentially all of the O4-producing cells segregated to the A2B5+PDGFαR+ fraction. Thus, whereas A2B5 can be viewed as enriching the fraction of glial progenitor cells, its utility appears to be a function of its harboring a significant subpopulation of PDGFαR+ cells, which themselves account for virtually the entire pool of oligodendrocyte-competent glial progenitor cells in the larger population.

Figure 2:
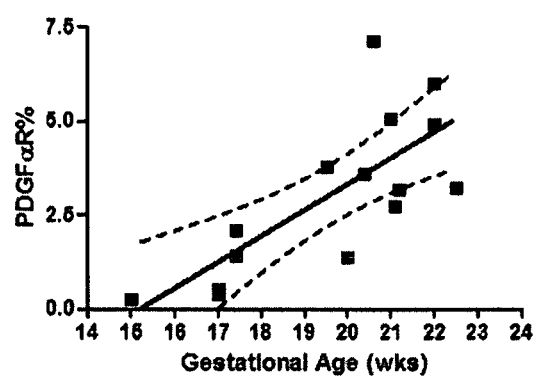
FIG. 2 is a graph showing the incidence of PDGFαR+ cells at various gestational ages in fetal human cortex. The solid line represents the linear regression of PDGFαR incidence with age ($r^2=0.57$), the dotted lines show the 95% confidence limits, indicating that most samples fall within these limits. Statistical testing further showed that the two parameters were significantly correlated (n=15, p=0.0012).

On this basis, it is concluded that the single-antigen sorted isolates of PDGFαR+ cells derived from fetal human forebrain tissue comprise a discrete population of oligodendrocyte-competent glial progenitor cells, free of contaminating neural phenotypes. These cells yield more predictable, higher efficiency oligodendrocyte differentiation and myelination than any human cellular vector yet described. For example, large numbers of PDGFαR-sorted glial progenitor cells from 18-21 week gestational age subcortical/cortical tissue were isolated (FIG. 2). This is an age range that harbors a substantial and expanding population of PDGFαR-defined progenitors.

Methods

Antibody Used for PDGFαR Isolation:

Anti-CD140a Mouse Monoclonal, IgG2a, clone alphaR1 (LaRochelle et al. (1993) Cell Growth Differ. 4:547-53), was used. This antibody was generated using a full-length expression plasmid (Matsui et al. (1989) Proc. Natl. Acad. Sci. USA. 86:8314-18) to transfect cells, which were then used to immunize mice from which a hybridoma was made. For flow cytometry and FACS, phycoerythrin (PE)-conjugated anti-CD140a (BD Cat No. 556002; Becton Dickinson, Franklin Lakes, N.J.) was used at 0.25 µg purified Ab/20 µl/million cells. For magnetic cell sorting (MACS), unconjugated anti-CD140a was used at 0.21 µg purified Ab/0.84 µl/million cells (BD Cat No. 556001; Becton Dickinson, Franklin Lakes, N.J.).

Analysis Protocol:

Fetal cells were gated according to forward and side scatter area measurements and subsequently gated on pulse height and width to discard doublet events. CD140a-PE positive events were determined following excitation at 488 nm and using emission measurements of 530/30 and 575/26 bandpass filters. Specific PE fluorescence was determined by measuring the increased 575/26 signal relative to 530/30 auto-fluorescence signal. Matched controls using IgG2a-PE antibody at the same control were used to set positive and negative gates.

FACS Example:

FIG. 1 shows a representative flow cytometry analysis for CD140a/PDGFαR cytometry. Fetal 21 week gestational age cortical tissue was dissociated and stained using CD140a antibody 24 hrs post dissociation. 3.8% of gated cells were positive for CD140a/PDGFαR. Using this gating schema shown for sorting, the resulting cell population is greater than about 99% pure as determined by IgG2a control staining.

PDGFαR Cells are Present in Fetal Cortex from 15 Weeks Gestational Age and Become More Abundant with Development:

The incidence of PDGFαR/CD140a cells was determined by flow cytometry in cortical dissociates from 15 fetal brains ranging from 15 weeks to 22 weeks. See FIG. 1B. Linear regression of PDGFαR incidence with age was determined ($r2=0.57$). Statistical testing further showed that the two parameters were significantly correlated ($n=15$, $p=0.0012$). The gating schema used for these values includes all PDGFαR positive events and may differ from the sort gates shown above. Taken together, these data show the incidence of PDGFαR increases with gestational age in fetal human cortex.

PDGFαR Cells can Also be Isolated from Fetal Ventricular Zone, Spinal Cord, Thalamus and Brain Stem:

Human PDGFαR expressing cells were found throughout the neuraxis in second trimester fetal brain. In addition to fetal cortex, PDGFαR+ cells were found in dissociates of the ventricular zone (1.1%, n=3, 17-18 wk), midbrain (3.8%, n=1, 16.2 wk), hindbrain (1.2%, n=1, 16.2 wk) and spinal cord (4.3%, n=1, 17 wk).

Expression of A2B5 or PSA-NCAM does not Correlate with PDGFαR Expression:

The human ventricular zone harbors a population of glial progenitors defined by the A2B5+/PSA-NCAM-phenotype. These cells generate very extensive amounts of myelination upon transplantation into the hypomyelinating shiverer mouse (Windrem et al., 2004, Nat Med 10(1):93-7). To assess whether the PDGFαR-defined presumptive OPCs were restricted to the A2B5+/PSA-NCAM-cell population, magnetic sorting was first performed for PSA-NCAM and collected both PSA-NCAM positive and negative fractions which were allowed to recover for 24 hrs. On the PSA-NCAM-fraction, double flow cytometry and FACS were performed for A2B5 and PDGFαR. As both PSA-NCAM and A2B5 are both recognized by mouse IgM antibodies, the PSA-NCAM+ fraction was performed on the basis of PDGFαR expression only. Using both isotype and fluorescence minus one (FMO) controls, PDGFαR-expressing cells were found not to be restricted to any specific A2B5 or PSA-NCAM defined phenotype (Table 1).

TABLE 1

| Sort | | | MARKERS | | | |
|---|---|---|---|---|---|---|
| MACS (%) | PSA-NCAM+ 57.3 ± 7.7% | | | PSA-NCAM− 42.8 ± 7.7% | | |
| FACS | PDGFαR+ | PDGFαR− | A2B5+ PDGFαR+ | A2B5+ PDGFαR− | A2B5− PDGFαR+ | A2B5− PDGFαR− |
| (%) | 4.1 ± 1.3% | 95.9 ± 1.3% | 5.2 ± 1.0% | 30.2 ± 6.1% | 3.8 ± 1.1% | 60.8 ± 5.5% |
| Overall % | 2.2 ± 0.7% | 54.9 ± 8.1% | 2.4 ± 0.8% | 12.9 ± 3.7% | 1.6 ± 0.5% | 26.0 ± 5.1% |

Breakdown of PDGFαR+ cells among A2B5 and PSA-NCAM sorted populations. The overall proportion of cells was calculated from the relative product of the relative frequencies of each pool (n = 4, 19-22 wks gestational age).

The majority of cells following sort were defined as PSA-NCAM+/PDGFαR− (54.9±8.1%); these accounted for more than half of all cells. The next most abundant population were cells that did not label for any of the three markers (PSA-NCAM/A2B5/PDGFαR; 26.0±5.1%). In contrast to these abundant pools, PDGFαR+ cells accounted then for only 6.2% of all cells scored.

To determine the phenotype of the sorted populations, cells were plated after sorting to encourage oligodendrocyte differentiation at low density in basal media supplemented with 0.5% platelet-depleted serum (pdFBS) and thyroid hormone (T3). 7 days after plating cultures were stained and counted for the major neural phenotypes, neurons, oligodendrocytes and astrocytes (Table 2).

TABLE 2

| | PDGFaR+ | | | PDGFaR− | | |
|---|---|---|---|---|---|---|
| | O4% | GFAP % | Tuj1% | O4% | GFAP % | Tuj1% |
| | | | PSA-NCAM+ | | | |
| | 8% (15/197) | 42% (76/180) | 26% (49/192) | 0% (0/208) | 40% (66/165) | 41% (74/182) |
| | | | PSA-NCAM−/A2B5+ | | | |
| | 15% (39/259) | 44% (88/2010) | 13% (29/224) | <1% (5/510) | 82% (210/255) | 5% (14/280) |
| | | | PSA-NCAM−/A2B5− | | | |
| | 10% (27/272) | 51% (114/222) | 5% (11/206) | 2% (10/490) | 77% (210/255) | 24% (56/234) |

Phenotypic characterization of triple sorted (±PDGFαR/A2B5/PSA-NCAM) cells, 7 DIV. Immediately post FACS, cells were plated onto substrate and cultured for 7 days in basal media (DMEM/F12/N2 + T3 and 0.5% pd-FBS). Cells were then stained for markers of differentiated astrocytes (GFAP), oligodendrocytes (O4), and neurons (TuJ1).

As previously shown (Windrem et al. (2004) Nature Medicine 10: 93-97), the proportion of TuJ1/bIII-tubulin-positive immature neurons was greatest in the PSA-NCAM+ PDGFαR− fraction (41%, n=1). Although GFAP+astrocytes were relatively abundant in all populations, the vast majority of PSA-NCAM-PDGFαR-both A2B5+ and A2B5− were astrocytic, greater than 75% (n=1). There were twice as many astrocytes in A2B5+/PSA-NCAM−/PDGFαR− cells than A2B5+/PSA-NCAM−/PDGFαR+.

The capacity of sorted cells to generate O4+ oligodendrocytes was almost entirely restricted to the three PDGFαR+ fractions regardless of either A2B5 or PSA-NCAM phenotype. There was over 10-fold greater percentage of O4+ cells in PDGFαR-positive fractions than PDGFαR-negative (O4%, PDGFαR+ vs. PDGFαR− two-tailed t-test, df=4, p=0.0098). Neither A2B5 nor PSA-NCAM significantly enriched or depleted the relative degree of O4-generation post-FACS.

PDGFαR-Sorted Cells Generate Oligodendrocyte and Astrocytes In Vitro:

Sorted PDGFαR cells were cultured at low density ($5 \times 10^5$/ml) in mitogenic conditions, PDGF-AA/FGF-2, to allow their expansion and measure the degree of spontaneous glial differentiation as either oligodendrocytes or astrocytes. By 5-7 days, small cells with elaborate fine processes and flat astrocytic-like cells appeared. These cells were stained at 7 days with phenotypic markers for glial progenitors (A2B5), immature oligodendrocytes (O4) and astrocytes (GFAP). The majority of cells remained as progenitors, 47.4±11.0% cells expressed the progenitor antigen A2B5 (n=5 fetal samples, SE). The rate of spontaneous oligodendrocyte differentiation in these conditions was relatively low, 4.8±1.5% O4+ cells at 7 days (n=7). In addition, only a few GFAP+ astrocytes (4%, n=1) were generated.

Withdrawal of FGF and addition of T3 significantly induced O4+ oligodendrocyte differentiation, 17.4±3.6% cells were O4+ at 7 days (p=0.023, unpaired t-test with Welch's correction, df=5). The number of cells remaining as A2B5-expressing progenitors was reduced by 18% relative to FGF/PDGF to 40.0±14.0% (n=4) from 58.7±15.4% (n=3). Addition of serum after sorting induced GFAP+ astrocytic differentiation. In cultures exposed to as low as 0.5% serum there was a 7-fold induction of astrocytic phenotype from 4% to 28% (n=1).

Oligodendrocyte Generation from Fetal Human Cortex was Restricted to PDGFαR+ Progenitors:

Oligodendrocyte differentiation in vitro was obtained when PDGFαR sorted progenitors were cultured in growth factor-free media containing T3; 37.63±6.5% of cells expressed the early oligodendrocyte marker O4+ (n=8) at 4 days in vitro. No significant difference was noted between FACS and MACS isolated cells (FACS-40.8% vs. MACS-32.3%, df=6, p=0.57).

Few PDGFαR negative cells generated oligodendrocytes after sorting, regardless of the culture conditions employed. In mitotic conditions of PDGF/FGF, 0.4±0.2% cells expressed O4 at 7 days in vitro (n=7). The majority of PDGFαR− cells were either TuJ1+ neurons (84%, n=1) or A2B5+ progenitors (20%, n=1). Application of various amounts of serum, up to 10%, or IGF did not significantly increase the percentage of cells expressing O4. Furthermore, when PDGFαR− cells were cultured in growth factor-free conditions, optimal for oligodendrocytic induction from PDGFαR+ cells, very few cells were found to express O4 at 4 days. The overall percentage was much less than 1% with only three O4 positive cells found among 1805 counted from 7 sorted fetal samples.

Example 2

A2B5/PSA-NCAM/CD11 Cell Sorting Strategy

Glial progenitor cells are isolated from dissociated tissue using a dual immunomagnetic sorting strategy. On the day after dissociation the cells are incubated with mouse anti-PSA-NCAM (Chemicon, Bellerica, Mass.) at 1:100 and with mouse anti-CD11, then washed and labeled with microbead-tagged rat anti-mouse IgM (Miltenyi Biotech, Auburn, Calif.), and removed by MACS depletion. The remaining PSA-NCAM-/CD11− cells are next incubated 1:1 with MAb A2B5 supernatant (clone 105; ATCC, Manassas, Va.), for 20 minutes, then washed and labeled with microbead-tagged rat anti-mouse IgM (Miltenyi Biotech, Auburn, Calif.). All incubations are done on ice (see Keyoung et al. (2001), Specific identification, selection and extraction of neural stem cells from the fetal human brain, Nature Biotechnology 19: 843-850; Roy et al. (2000), In vitro neurogenesis by progenitor cells isolated from the adult human hippocampus, Nature Med. 6: 271-277.)

Magnetic separation of A2B5+ cells (MACS; Miltenyi, Auburn, Calif.) is then performed, as described (Nunes et al. (2003), Identification and isolation of multipotential neural progenitor cells from the subcortical white matter of the adult human brain, Nature Medicine 9: 439-447). The bound cells are then eluted, yielding a highly enriched population of A2B5+/PSA-NCAM-/CD11− cells. After sorting, the cells are maintained in vitro for 1-2 days in DMEM/F12/N1 with 20 ng/ml bFGF, then frozen and stored in liquid nitrogen, at $2 \times 10^6$ cells/ml in 7% DMSO/93% FBS.

Example 3

Cell Therapy Rescue of a Congenital Leukodystrophy Methods

Cells:

Fetal OPCs were extracted from second trimester human fetuses (19 to 22 weeks gestational age, g.a.), obtained at abortion as described (Windrem et al., 2004 Nature Medicine 10: 93-97.). The forebrain ventricular/subventricular zones were dissected from the remaining brain parenchyma, the samples chilled on ice, and the minced samples then dissociated using papain/DNAse as described (Keyoung et al., 2001), within 3 hours of extraction. The dissociates were maintained overnight in minimal media of DMEM/F12/N1 with 20 ng/ml FGF. A total of 5 tissue samples (1 at 19 wks g.a., 1 at 20 wks, 3 at 22 wks) were used for this study, all from chromosomally normal fetal donors.

Sorting:

Glial progenitor cells were isolated from dissociated tissue using a dual immunomagnetic sorting strategy. On the day after dissociation the cells were incubated with mouse anti-PSA-NCAM (Chemicon, Bellerica, Mass.) at 1:100. then washed and labeled with microbead-tagged rat anti-mouse IgM (Miltenyi, Auburn, Calif.), and removed by MACS depletion. The remaining PSA-NCAM-cells were next incubated 1:1 with MAb A2B5 supernatant (clone 105; ATCC, Manassas, Va.), for 20 minutes, then washed and labeled with microbead-tagged rat anti-mouse IgM (Miltenyi, Auburn, Calif.). All incubations were done on ice. Magnetic separation of A2B5+ cells (MACS; Miltenyi, Auburn, Calif.) was then performed, as described (Nunes et al., 2003, Nat Med. 9(4): 439-47). The bound cells were then eluted, yielding a highly enriched population of A2B5+/PSA-NCAM-cells. After sorting, the cells were maintained in vitro for 1-2 days in DMEM/F12/N1 with 20 ng/ml bFGF, then frozen and stored in liquid nitrogen, at $2 \times 10^6$ cells/ml in 7% DMSO/93% FBS.

Transplantation and Husbandry:

Homozygous shiverers were crossed to homozygous rag2 null immunodeficient mice (Shinkai et al., 1992), to generate a line of shi/shi×rag2−/−myelin-deficient, immunodeficient mice. Newborn pups of this line were transplanted within a day of birth, using a total of 300,000 donor cells dispersed over 5 injection sites. The pups were first cryoanesthetized for cell delivery. $5 \times 10^4$ donor cells in 0.5 µl HBSS were then injected at each of 4 locations in the forebrain subcortex, specifically into the anterior and posterior anlagen of the corpus callosum bilaterally. These injections were delivered to a depth of 1.0 to 1.2 mm ventrally, depending on the weight/size of the pup (which varied from 1-1.5 g). A fifth injection of $10^5$ cells in 1 µl was delivered into the cerebellar peduncle dorsally, to gain access to the major cerebellar and dorsal brainstem tracts. All cells were injected through pulled glass pipettes, inserted directly through the skull into the presumptive target sites. The pups were then returned to their mother, until weaning at 21 days; at that point, each litter was moved to separate enriched housing.

Survival Analysis and Statistics:

Kaplan-Meier analysis was used to assess the different survivals of transplanted and control mice, as described (Hosmer and Lemeshow, 1999, Applied Survival Analysis (New York, John Wiley and Sons). No difference in survival was observed between saline-injected and untreated mice, so the two populations were combined as a single control population for the Kaplan-Meier comparison with GPC-implanted mice.

Analyses of variance (ANOVA) were performed using GraphPad Prism® (v4.0c for Macintosh®; GraphPad Software, San Diego, Calif.).

Immunolabeling:

Human cells were identified with mouse anti-human nuclei, clone 235-1 at 1:100 (MAB1281, Millipore, Billerica, Mass.). Myelin basic protein was labeled with rat anti-MBP at 1:25 (Ab7349, Abcam, Cambridge Mass.), and axons with mouse anti-neurofilament cocktail at 1:1000 (SMI-311 and -312, Covance, Princeton, N.J.). Monoclonal antibodies against Caspr, Nav1.6 and Kv1.2 were used at 1:600, 1:200 and 1:200, respectively, and were obtained from NeuroMab (Davis, Calif.). Rabbit anti-Caspr and anti-βIV spectrin were generated as described (Rasband and Trimmer, 2001, Developmental clustering of ion channels at and near the node of Ranvier. Dev Biol 236: 5-16; Yang et al., 2007, βIV spectrin is recruited to axon initial segments and nodes of Ranvier by ankyrinG, J Cell Biol 176: 509-519), while rabbit anti-Caspr2 was obtained from Millipore. Rabbit anti-olig2 was obtained from Abcam (Cambridge, Mass.) (Ab33427) and used at 1:1,500. Alexa Fluor® secondary antibodies, goat anti-mouse, rat, and rabbit 488, 568, 594 and 647 were used at 1:400 (Invitrogen, Carlsbad, Calif.).

Myelinated Axon Counts:

Uniform random sagittal sections of the cervical spinal cord, and coronal sections of the corpus callosum, were both selected for neurofilament and MBP staining; in the spinal cord samples, the most medial sections were analyzed with respect to the percentage of myelinated host axons. A 1 µm stack of 10 superimposed optical slices taken at 0.1 µm intervals (Olympus FluoView® 300; Olympus Optical, Melville, N.Y.) was made for each of 3 fields of view in the dorsal columns, beginning rostrally and progressing caudally. Three parallel, equidistant lines were laid over the images perpendicular to the axons. Axons were scored at intersections with the lines as either myelinated (closely apposed to myelin basic protein (MBP) on both sides) or unmyelinated. This procedure was then repeated for the coronally-cut samples of corpus callosum.

Proportionate Representation of Donor Cells.

The percentage of human cells in the recipient white matter was assessed as a function of time after transplantation. Randomly initiated, uniformly sampled sagittal sections of the brains were labeled for human nuclei and DAPI (Vector Labs, Burlingame, Calif.). 4-6 sections (depending on the persistence of the structure in the selected range of sections) of the corpus callosum, fimbria, and cerebellar white matter were counted, with data entry and reconstruction using BioQuant Image Analysis (Nashville, Tenn.). All human nuclei and DAPI-labeled cells in the white matter regions of these 14 µm sections were counted.

Electron Microscopy:

The four mice that survived over a year were perfused transcardially with HBSS, followed by 4% paraformaldehyde with 0.25% glutaraldehyde and 6% sucrose in phosphate buffer (sucrose-PB). One hemisphere of each brain and longitudinal half of each spinal cord were post-fixed in 2% paraformaldehyde, 2.5% glutaraldehyde in sucrose-PB for electron microscopy; the other half of each brain and spinal cord were post-fixed in 4% paraformaldehyde in sucrose-PB for immunohistochemistry. Tissue samples used for electron microscopy were osmicated, dehydrated in ethanol, and embedded in Epon. Ultrathin sectioning was performed using a PowerTome® X Ultramicrotome (RMC products by Boeckeler, Tucson, Ariz.). The ultrathin sections were collected on formvar-coated copper one-hole grids and contrasted with lead citrate and uranyl acetate, then examined in a JEOL (Tokyo, Japan) 100CX transmission electron microscope.

Seizure Counts:

Mice were placed in a sterilized Plexiglass cage with a camera embedded in the ceiling (PhenoTyper, Noldus, Wageningen, the Netherlands) and left undisturbed overnight while their movements were recorded by infra-red light. Six non-overlapping half-hour video segments were randomly selected from each 8 hour videotape, excluding the first 3 hour segment so as to diminish any effects of the novel environment. Two segments for each mouse scored were assigned to each of 3 observers, blinded as to the mouse's age and treatment. The observers recorded and timed each mouse's seizures, which were defined as such when the mouse fell to its side and assumed a rigid, stereotypically tonic posture, typically complicated by clonic flexion-extension of the trunk and limbs. A seizure was timed as ending when the mouse first moved to right itself. The number of seizures per hour, and the total ictal time per hour, were thereby scored.

Transcallosal Transmission:

Mice were anesthetized with ketamine (60 mg/kg, i.p.) and xylazine (10 mg/kg, i.p.), intubated through a tracheotomy and ventilated with a ventilator (SAR-830, CWE, Inc., Ardmore, Pa.). A femoral artery was catheterized for monitoring mean artery blood pressure and blood gases, and body temperature was maintained at 37° C. by a warming blanket (Harvard Apparatus, Holliston, Mass.). Mice were secured with a custom-made metal frame that was glued to the skull with acrylic cement. Two burr holes, each 3 mm in diameter, were made bilaterally, centered 1-2 mm posterior to bregma and 2-3 mm from the midline. The dura was removed and agarose (0.75% in saline) was poured into the craniotomy sites, which were then closed with a 0.17 mm thick glass coverslip. The head frame was then attached to a second frame that was coupled to the microscope stage. Glass micropipettes filled with 2M NaCl solution were then inserted to a depth of 200 µm into the right cortex, at 1.5 mm posterior to bregma and 2.5 mm from the midline, for recording the local field potentials (LFPs) generated by transcallosal electric stimulation. Electrical stimulation (100 µs at 10-1000 µA, via an ISO-Flex isolator controlled by a Master-8 programmer; AMPI, Israel) was applied using a bipolar electrode inserted at the same coordinates in the contralateral (left) hemisphere. Evoked LFPs were recorded by a multiClamp 700A amplifier, filtered at a cutoff frequency of 1 kHz, and sampled at an interval of 200 µs by a pCLAMP 9.2 program and DigiData 1332A interface (Axon Instruments Inc., Foster City, Calif.). The same electrode was used to continuously monitor the electrocorticogram (ECoG). ECoG was recorded continuously by a multiClamp 700A Amplifier (Axon, Foster City, Calif.) with a low frequency filter at 1 Hz and high frequency filter at 100 Hz (51, 52), and a pCLAMP 9.2 program and DigiData 1332A interface (Axon, Foster City, Calif.) with an interval of 200 µs. The amplitude of stimulus-evoked transcallosal response was then calculated as the difference between the peak and baseline, whereby the baseline was defined as the average potential measured during the 20 ms before the stimulation was delivered. The velocity of transcallosal response was calculated, together with the latency of the response and the distance between the stimulating and recording electrodes. The response latency was defined as the difference between the stimulus start and the peak. Two recordings of the transcallosal responses to electric stimulation (0.10 ms, 0.01-0.10 mA) were obtained from each animal.

Results

Engrafted Shiverer Mice Exhibited Substantially Prolonged Survival:

Newborn double-homozygous shiverer (shi/shi)×rag2−/− immunodeficient mice were implanted with either 300,000 human glial progenitor cells (GPCs) (n=26), with PBS vehicle control (n=29), or with nothing (n=59). Cells were delivered at 5 sites, including the anterior and posterior corpus callosa bilaterally, and the presumptive cerebellar peduncle as a single midline injection; PBS controls received equal volume injections at each site, while the no-injection controls were not injected. The mice were then returned to their mothers, and allowed to develop normally, with weaning at 21 days and small group housing thereafter. All mice were observed to undergo progressive neurological deterioration, typically first manifest by a progressive truncal instability worse upon ambulation, followed with marked hindlimb weakness by 14-16 weeks of age, and seizures beginning at 4-6 weeks but rapidly increasing in frequency by 18-19 weeks. Thus, by 18 weeks, all mice exhibited markedly impaired forward ambulation, and frequent episodes of sustained seizures. Over a range of 130-150 days postnatally, all of the 29 PBS-treated and 53 untreated control shiverer mice died, with median and mean (±SE) survivals of 135.0±1.4 and 132.4±2.1 days, respectively.

In sharp contrast, of the 26 implanted mice, 20 died during this period, but 6 (23.1%) survived. Whereas the average survival of the untreated controls approximated 130 days, and none of the 82 total control mice survived to 150 days, these 6 implanted mice survived over 160 days, and 4 appeared to have been rescued, surviving over a year before being sacrificed for analysis. These mice exhibited overtly improved neurological function, with decreased seizure incidence and improved mobility and self-care. Indeed, transplanted mice surviving beyond 190 days exhibited apparent treatment-dependent cure, with sustained survival over a year, accompanied by a virtually complete recovery of normal neurological phenotype. As a result, the engrafted mice as a group exhibited significantly prolonged survival:

Kaplan-Meier analysis (Hosmer and Lemeshow, 1999) confirmed that the treatment-associated improvement in survival was statistically significant, and profoundly so (p=0.0003; hazard ratio=0.4718 (95% CI=0.30-0.70)

Transplantation was Associated with Neurological Improvement and Diminished Seizures:

The rescued mice exhibited substantial resolution of their neurological deficits. Shiverer mice typically exhibit truncal instability and marked intention tremor, evident within weeks of birth, which becomes complicated by a progressive hindlimb weakness, and multimodal sensory and perceptual deficits that include blindness, such that by 18-19 weeks of age they are severely impaired. In addition, they manifest a progressively worsening seizure disorder, often succumbing to status epilepticus. Those mice that survived the period spanning 130-150 days postnatally, exhibited noticeable improvement in their neurological exams thereafter, manifest by 7-8 months of age as diminished frequency of seizures and improved ambulation, with more forward motion and less retropulsion or freezing. Over the several months thereafter, the transplanted mice incrementally improved, regaining normal fluidity in ambulation, normal voluntary explorative behavior, and less truncal intention tremor. All 5 mice surviving to at least 35 weeks of age were substantially normal by that point and thereafter in terms of their grossly assessable neurological function, save for a coarse axial intention tremor, manifesting as a wobble on forward ambulation.

The frequency and duration of spontaneous seizures was assessed in both untreated and transplanted shi/shi×rag2 nulls, as a function of age; with special attention to the incidence of seizures in transplanted mice that were rescued by transplant, compared to their treated counterparts that nonetheless succumbed. The first seizures of shiverer mice—typically characterized by absence-like episodes of tonic akinesia, followed by a rapid evolution to brief tonic-clonic events—appeared by 35-42 days of age. At approximately 120 days, the incidence of seizures was noted to substantially increase, in both treated and untreated animals alike. Over the period spanning 120-140 days, the seizure incidence of each group increased, yielding frequent seizures every hour; these ictal events progressed to sustained periods of status epilepticus, often associated with death. However, in those animals that survived this period to enjoy long-term survival, seizure incidence fell dramatically, such that no seizure activity whatsoever was observed at 12 months (p<0.0001 by 1 way ANOVA, separately comparing 12 month transplanted animal seizure incidence to that of 4 month transplanted and control shiverers). Thus, perinatal glial progenitor cell (GPC) transplantation was associated with markedly diminished seizure activity in those shi/shi× rag2 null mice that were rescued by perinatal transplantation, such that by a year, none manifested any residual spontaneous seizure activity, while otherwise exhibiting virtually complete neurological recovery.

Besides spontaneous seizures, shiverers exhibited stimulus-evoked seizure activity that increased in both frequency and duration as a function of age. To quantify this pathological response to handling, a brief screening test was established by which mice were briefly and abruptly suspended by the tail, and their behavioral responses observed. Such tail suspension was sufficient to induce seizures in a large proportion of shiverer mice, whether treated or not, by 3 months of age. The induction of seizure activity within 30 seconds of tail suspension was thus chosen as a metric by which to assess the effect of cell transplant on seizure incidence and duration. Among the transplanted mice that survived at least 5 months, 47±2.8% of tail suspension challenges resulted in seizures. In contrast, by 8 months, none of the 4 surviving mice could be induced to seize by tail suspension. Linear regression of the percentage of mice induced to seize, plotted against their age in days, revealed a best-fit of y=−0.324x+116.7. Regression analysis confirmed that the negative correlation between seizure incidence and age (r=0.826; r2=0.68) was significant (p<0.0001; F=53.68 [1, 25 d.f.]).

Perinatal Grafts of Human Glial Progenitors Yield Widespread and Dense Host Myelination:

To assess the terminal distribution of donor cells and robustness of myelination in the transplanted animals, and to compare the extent of donor cell dispersal and myelination between short- and long-term survivors, the latter were ultimately sacrificed at 13 months of age, after assessment of their transcallosal conduction velocities and seizure frequency. The brains and spinal cords of these mice were then analyzed in terms of donor cell distribution and density, myelin production and the proportion of myelinated axons, nodal architecture and reconstitution, and ultrastructural metrics including myelinated axons, and myelin G-ratios. Each of these metrics was then compared to those obtained from transplanted mice that had died earlier, as well as to unimplanted shiverer controls, as well as to wild-type, normally myelinated rag2 null mice.

These histological data supported the compelling nature of the survival data. Human donor cell engraftment was extraordinarily extensive, with essentially whole neuraxis penetration and colonization by the human donor OPCs. High donor cell densities were observed throughout the forebrain, cerebellum, brainstem and cervical spinal cord, diminishing only at the level of the thoracolumbar cord, yet increasing again in the sacral cord and conus medullaris. The pattern of myelination, as indicated by MBP expression, reflected this widespread engraftment, with equally widespread and dense myelination, including not only all major central white matter tracts, but also structures as distant and diverse as the cranial ganglia, optic chiasm and conus medullaris. These long-term survivors, whose neurological exams had largely normalized by 9 months of age, exhibited essentially complete myelination of the brain, brainstem and cerebellum, with substantial myelination of the optic nerves, spinal cord, and spinal roots, as well as of the cranial roots and ganglia. In regards to the latter, the cessation of donor GPC migration at the border of CNS and PNS was striking, such that donor-derived myelination occurred up to, but not beyond, the transition points demarcating central ganglia and roots from peripheral nerve. The resultant densities and patterns of donor cell dispersal resulted in the virtually complete chimerization of the murine hosts' central nervous systems, which thereby acquired a largely humanized white matter. Three-dimensional reconstructions confirmed that both the pattern and density of donor-derived myelination in the brains of transplanted shiverers approximated that of wild-type, normal mice.

Xenografted Shiverer Brains Exhibit Restored Nodes of Ranvier:

Donor cell-derived myelination of shiverer axons was accompanied by the acquisition of normal nodes of Ranvier and paranodal structure. Using high-resolution confocal imaging of the corpus callosa, cervical spinal cords, and optic nerves of implanted shiverers killed at 35 or 52 weeks of age, the distribution pattern was assessed for the paranodal and juxtaparanodal proteins Caspr and the KV1.2 voltage-gated potassium channel, respectively, the contiguous interaction of which characterizes the normal node of Ranvier (Rasband and Trimmer (2001) Dev Biol 236: 5-16.; Schafer and Rasband (2006) Curr Opinion in Neurobiology 16: 508-514). These potassium channels are assembled at—and functionally define—the juxtaparanodes in myelinated axons, but they are broadly and nonspecifically expressed in unmyelinated fibers (Rasband and Trimmer, 2001). In addition, the axonal expression and compartmentalization of NaV1.6 fast sodium channels, which are typically sequestered at nodes of Ranvier in intact myelinated axons, but dispersed broadly along unmyelinated or dysmyelinated fibers, was determined. Similarly, immunostaining for βIV-spectrin, which couples to ankyrin to organize fast sodium channels at the node of Ranvier, and hence typically coincides with nodal Nav1.6 expression, was performed (Schafer and Rasband, 2006; Sherman and Brophy (2005) Nature Rev Neurosci 6, 683-690; Yang et al. (2007) J Cell Biol 176: 509-519.

Using these complementary nodal markers, an essentially normal organization of the nodes of Ranvier was observed in transplanted mice, which was indistinguishable from that of wild-type mice. Caspr and KV1.2 were expressed in organized paranodal and juxtaparanodal apposition, with an expression pattern that contrasted sharply with the grossly uncoordinated pattern of diffuse Caspr and KV1.2 immunolabeling that was evident in the untransplanted controls. Similarly, both NaV1.6 and βIV-spectrin identified nodes of Ranvier in the transplanted shi/shi mice, flanked by Caspr defining the paranodes, whereas their untransplanted controls showed no such sequestration of either NaV1.6 or βIV-spectrin expression. Thus, despite interspecies chimerization, the glio-axonal interactions of human GPC-derived oligodendrocytes with host mouse axons were functionally appropriate. More broadly, GPC-derived oligodendrocytes were able to communicate effectively with host axons, organizing structurally appropriate nodes of Ranvier while sequestering fast sodium channels within the nodes, and thereby myelinating their axonal substrates both effectively and appropriately.

Transcallosal Conduction Velocities are Restored in Xenografted Shiverer Brains:

In light of the apparent histological reconstitution of normal myelin, donor OPC-derived myelin was assessed in both extent and functional competence to determined whether it restored the conduction speed of newly myelinated central axons. To this end, the conduction velocity was assessed across the corpus callosum in a sample of 4 long-surviving transplanted shiverer mice, between 12 and 13 months after neonatal xenograft. The transcallosal nerve conduction velocities were determined by recording response amplitudes and times from depth electrodes placed at several sites in the corpus callosa of each of these mice, after contralateral stimulation at symmetric sites during open craniotomy. Equal numbers of age-matched wild-type (congenic C3h) mice and rag2-null controls were assessed identically, as was a necessarily younger (4 months-old) sample of untransplanted shiverer×rag2 null mice. As this was a terminal procedure, these animals—all of which had exhibited not only sustained survival but also a substantial restoration of normal neurological function—were sacrificed after measurement of their transcallosal conduction velocities, thus ending the survival study in which they were subjects.

Whereas both control Fvb wild-type (n=3) and rag2 null C3h mice (n=4) exhibited conduction velocities of 0.324±0.01 and 0.328±0.03 m/sec respectively, the shiverer×rag2 mice (n=4), also on the C3h background, exhibited substantially slower conduction, at 0.260±0.02 m/sec. In contrast, transplanted shiverer×rag2 mice, tested just prior to sacrifice 12-13 months post-transplant (n=3), had an average conduction velocity of 0.330±0.01 m/sec. Repeated measures ANOVA with post hoc Boneferroni t tests revealed a significant treatment effect (F=35.15 [3, 9 df]), such that callosal conduction by the transplanted mice was significantly faster than untransplanted shiverer×rag2−/−mice (p<0.001), and indistinguishable from that of normally myelinated Fvb wild-type and rag2 null mice. The more rapid transcallosal conduction exhibited by the transplanted mice was sustained across stimulus intensities, and thus appeared to represent improved conduction across a wide spectrum of fiber diameters. Thus, neonatal transplantation of human OPCs yielded sufficient myelin, in terms of both density and physiological competence, to restore normal inter-hemispheric conduction velocity to a major central tract, the corpus callosum.

Myelination and Axonal Ensheathment were Progressive Over Time:

The brains of transplanted shiverers at 18-20 (n=10), 27 (n=1), 35 (n=1) and 52-56 (n=4) weeks of age were assessed for the distribution pattern and densities of human donor cells, as well as of donor-derived myelin, in these recipient brains. (The 20 week-olds had died natural deaths despite their extensive donor cell engraftment, while the 52-56 week-olds were long-survivors, which had been killed to allow histological analysis. The deaths of the 27 and 35 week-old mice—natural and accidental deaths, respectively—provided informative, if singular, intermediate time points.)

Whereas cerebral and cerebellar myelination, as followed by MBP expression, were both substantial and geographically widespread at 20 weeks, both the density and distribution of MBP expression in the brainstem and cervical spinal cord were more extensive at 35 weeks than 20, and much more so at 52-56 weeks. In particular, the 52-56 week-old transplanted mice exhibited essentially complete myelination of the brainstem, whereas the 20 week-olds still exhibited a number of regions of relative hypomyelination relative to wild-type controls. The areas of relatively delayed myelination included the ventral long tracts of the brainstem, as well as the brainstem tegmentum and intrinsic internuclear tracts, all of which were more extensively myelinated at 52 weeks of age than at earlier time-points. By scoring the proportion of ensheathed host axons in confocal optical sections immunostained for MBP and neurofilament, it was determined that by 52 weeks, 78.0±4.8% of axons in the cervical corticospinal tract at the cervico-medullary junction were myelinated, only a marginally smaller proportion than that observed in wild-types (93.9±0.9%). At that same timepoint, the proportion of myelinated axons in both the corpus callosum and corticospinal tract of the transplanted animals was indistinguishable from that of their wild-type controls; each exceeded 60%. Using transmission electron microscopy (TEM), concentrating on the longitudinal and largely parallel fibers of the cervical spinal cord, the criteria were validated that defined myelin-ensheathed axons in the confocal analysis. TEM of the cervical corticospinal tract of 12-13 month-old transplanted shiverers established that the majority of axons manifested ultrastructurally normal myelin, with both major dense lines and multilayer lamination, thereby confirming that axons which appeared ensheathed in confocal optical sections were indeed so. Furthermore, the major dense lines of the observed myelin indicated its necessarily donor cell origin, since shiverer oligodendrocytes do not make major dense lines, as formation of the latter require myelin basic protein—in which shiverers are genetically deficient (Readhead et al. (1990) Cell 48: 703-712.). In addition, the calculated G-ratio, defined as the ratio of axonal diameter to total myelin-ensheathed fiber diameter, was significantly higher in the untreated shiverers than in either transplanted shiverers or wild-type rag2 nulls, while the latter groups did not differ from one another. This indicated that, whereas untreated shiverers had little or no myelin ensheathment, their transplanted kindreds had myelin sheaths as thick, on average, as their normally-myelinated wild-type×rag2 null controls.

The progressive myelination of transplanted shiverers did not appear to be a function of the rate or kinetics of donor cell dispersal, in that the topography of donor cells at 35 weeks did not differ substantially from that observed at 52 weeks. Nonetheless, the local densities of donor-derived cells did appear to rise over time; this rise was asymptotic, which appeared to reflect the fall in mitotic competence of the donor cell pool following their initial expansion in the first half-year or so after transplantation. Thus, long after human donor cells achieve their destinations, myelinogenesis and axonal ensheathment continue to progress slowly, ultimately achieving the myelination of the recipient neuraxis after a protracted period of postnatal maturation; this may reflect the incremental engagement of local axons by single oligodendrocytes, as the latter mature and expand their individual domains of myelin ensheathment, adding axons to their ensheathed cohort one at a time over a period of many months.

Long-Term Survival was Associated with Humanization of the Recipient White Matter:

The selective expansion of the human glial population in the shiverer mouse white matter appears to be at least in part a product of the more sustained proliferation of the transplanted human GPCs, which as derived from the late second trimester fetal subventricular zone, would be expected to have continued actively dividing for at least another 9-12 months, assuming cell-autonomous regulation of expansion potential. Accordingly, when the number of all human cells in the recipient mouse brains were plotted as a function of time, the initial dose of 300,000 cells/recipient had expanded to an average of 12 million human donor glia by 12-14 months in the long-term survivors. When the incidence of Ki67+ cells was assessed in three sample regions—the corpus callosum, fimbria and cerebellar white matter—the fraction of mitotic human donor cells was found to be much higher than that of the local host cells, both perinatally and for many months thereafter; only at a year after engraftment was the Ki67+ fraction of human donor cells observed to fall below 2%. Even then, the fraction of Ki67+ human glia remained higher than the corresponding proportion of Ki67+ mouse cells, in both the transplanted hosts, and in the rag2 wild-type or shi/shi×rag2−/−mouse controls (F=12.42 [3, 2 df] by 2-way ANOVA permuting cell type and region; $p<0.05$ for each comparison, by Boneferroni post hoc t tests). Ultimately though, despite the preferential expansion of the human donor cell pool, its relative mitotic quiescence was achieved by a year after transplantation, according to the approximate time course by which normal human GPCs attenuate their expansion in situ. Importantly in this regard, no evidence of heterotopic foci, anaplasia or neoplastic transformation was ever noted in over 100 transplanted mice serially examined.

These data indicate that donor human GPCs exhibit more robust and sustained mitotic expansion than their host murine counterparts after transplantation, and that over time, this results in the relative humanization of the recipient white matter. Indeed, quantification of the human donor cell complement revealed that in 4 long-surviving transplanted mice sacrificed at 12-14 months, at least a third of all cells in the corpus callosum, fimbria and cerebellar white matter were of human origin (35.3±11.8%, 42.9±10.9%, and 40.8±6.9%, respectively). In 3 of the 4, over 40% of all cells in each of these white matter regions were human, and in the densest engraftment among these, that of a mouse sacrificed at 13 months, 54.6% of all cells in its callosum were human. Since just under a third of all cells in the shiverer white matter are non-glial—these include microglia, endothelial cells, and pericytes—at least 80% of all callosal glial cells in this "best-case" mouse were estimated to be of human origin by a year after engraftment; more broadly, over half of all callosal glia were human in each of the long-surviving recipients assessed.

Example 4

CD140a-based FACS Isolates a Transcriptionally-distinct Myelinogenic Fraction of Glial Progenitor Cells from the Fetal Human Forebrain Methods Cell and Tissue Samples:

Fetal brain tissue was obtained from 38 cases (15-22 weeks gestational age). Cortical tissue was dissected into ventricular and sub-ventricular zone and overlying cortical mantle and chilled on ice. Briefly, the minced samples were dissociated using papain and DNase (see Windrem et al. 2004, Nat. Med. 10(1): 93-7, which is incorpotated by reference at least for the methods and compositions described therein), within 2 h of extraction, and maintained overnight in DMEM/F12/N1 with 20 ng/ml FGF-2 (Sigma Aldrich, St. Louis, Mo.).

Sorting:

The day after dissociation, cells were prepared for either magnetic separation or FACS. PSA-NCAM-defined depletion of cells by magnetic separation was performed (see Windrem et al. 2008, Cell Stem Cell s(6): 553-65, which is incorporated by reference at least for the methods and compositions described therein). For PDGFαR or CD9 FACS, cells were resuspended in PBS with 2 mM EDTA and 0.5% BSA and incubated with primary antibody. Isotype and fluorescence-minus one controls were used to set appropriate gates. Single cells were discriminated using pulse width and height measurements. After sorting, cells were maintained in DMEM/F12/N1 for up to 14 days. For transplantation cells, were maintained in FGF-2 for 1-3 days.

Immunocytochemistry:

In vitro cultures were stained for the early progenitor and oligodendrocyte markers, A2B5 and O4 respectively (see Roy et al. 1999, J. Neurosci 19(22) 9986-95 and Sim et al. 2006, Ann. Neurol. 59(5): 763-79, which are incorporated by reference at least for methods and compositions described therein). Both O4 and A2B5 were localized on live cells that were then fixed with 4% paraformaldehyde. O4 supernatant was used at a dilution of 1:100, and monoclonal antibody A2B5 supernatant (clone 105, American Type Culture Collection) was diluted in a 1:1 with DMEM/F12/ N1, each was applied for 40 minutes at 4° C. Post-fixation, cultures were stained for astrocyte markers, GFAP (1:1000, Chemicon, Bellerica, Mass.) and AQP4 (1:200, Chemicon, Bellerica, Mass.), and for neuronal markers, βIII-tubulin (clone TuJ1, 1:1000, Covance, Princeton, N.J.) and HuD (clone 16A11, 10 ng/ml, Invitrogen, La Jolla, Calif.). Oligodendrocyte lineage cells were labeled using Olig2 (1:200, AbCam, Cambridge, Mass.). Neural progenitor cells were labeled using anti-SOX2 antibody (1:500, R & D Systems, Minneapolis, Minn.). Secondary antibodies, Alexa-488, 594 and 647 conjugated goat-anti mouse IgM, rabbit and rat antibodies respectively were used at a dilution of 1:400 (Invitrogen, La Jolla, Calif.). Fixed cultures were counterstained with DAPI (10 ng/ml; Invitrogen, La Jolla, Calif.).

Scoring:

The number of phenotypically labeled cells were counted in 10 randomly chosen fields from individual replicate samples (n=3 at each dosage level). Statistical significance was assessed by one-way repeated measures analysis of variance (ANOVA), followed by Dunnett's multiple comparisons test (GraphPad Prism® 5 (Graph Pad Software, Inc., La Jolla, Calif.), p<0.05).

Immunohistochemistry in Sections:

Transplanted cells were identified using antibody 1281 to human nuclei (1:400, Chemicon, Bellerica, Mass.), monoclonal antibody 2029 (clone 9.2.27) to human chondroitin sulfate proteoglycan Ng2 (1:200, Chemicon, Bellerica, Mass.), goat antibody to human Olig2 (1:200, R&D Systems, Minneapolis, Minn.), rabbit antibody 5804 to GFAP (1:1000, Chemicon, Bellerica, Mass.), rabbit antibody to Ki67 (1:200, LabVision, Fremont, Calif.), and rat antibody 7349 to MBP (1:25, Abcam, Cambridge, Mass.) (see Nunes et al. 2003, Nat. Med. 9(4):439-47; Windrem et al. 2004, Nat. Med. 10(1):93-7; Windrem et al. 2002, J. Neurosci. Res. 69(6):966-75; and Windrem et al. 2008, Cell Stem Cell 2(6): 553-65, which are incorporated by reference at least for the methods and compositions described therien). Confocal imaging was done using an Olympus Fluoview® (Center Valley, Pa.) mated to an IX70 inverted microscope. Argon laser lines were used to achieve three-channel immunofluorescence detection of Alexa488-,568- and 647-tagged goat or donkey secondary antibodies (each 1:400, Invitrogen, La Jolla, Calif.). Ng2 immunofluorence was obtained following incubation with biotinylated secondary antibody (1:200, Jackson ImmunoResearch Laboratories, West Grove, Pa.), and avidin-Alexa488 (1:500, Invitrogen, La Jolla, Calif.). Three sections at least 350 μm apart were counted Stereo Investigator, MicroBright Field, Williston, Vt.), representing the rostral, middle, and caudal regions of fibria and corpus callosum white matter engraftment for each animal.

Transplantation and Tagging:

Homozygous shiverer mice were bred. Within 1-2 days of birth, pups were cryoanesthetized for cell delivery. Donor cells ($0.5 \times 10^5$) in 1 μl of HBSS were injected through a pulled glass pipette and inserted through the skull into the presumptive corpus callosum. Transplants were directed to the corpus callosum at a depth of 1.0-1.2 mm, depending on the weight of the pup, which varied from 1.0 to 1.5 g. Pups were killed at 8 and 12 weeks thereafter. To prevent rejection of xenografts, pups were injected daily with an immunosuppressant FK-506 (5 mg/kg, Tecoland Inc, Edison, N.J.) after reaching 2 weeks of age.

Real-Time RT-PCR Low Density Array Analyses:

Six fetal samples were FACS sorted for CD140a/PDGFαR (21-22 weeks gestational age) and positive and negative fractions collected for molecular analysis. Total RNA was extracted using RiNeasy® (Qiagen, Chatsworth, CZ) and amplified using ribo-SPIA based whole transcriptome based-amplification (NuGen, San Carlos, Calif.). The expression of 47 cell type-specific marker genes was assessed using a 48 gene low-density Taqman® based array (TLDA, Applied Biosystems, Foster City, Calif.). The relative abundance of transcript expression was calculated by $\Delta\Delta C_t$ analysis, and the expression data normalized to GAPDH. Genes whose expression was not detected in the more than half of the RNA samples were excluded. Statistical analysis was performed on $\log_2$-transformed data and p-values were corrected for multiple testing using false-discovery rate (see Hochberg and Benjamini 1990, Stat. Med. 9(7):811, which is incorporated by reference at least for the methods and compositions described therein).

Microarray:

Extracted total RNA was amplified using 3'-biased ribo-SPIA (NuGen Ovation®, San Carlos, Calif.) and hybridized onto Affymetrix (Santa Clara, Calif.) U133+2 arrays according to manufacturer's instructions. Raw cell intensity data (CEL) data were processed using the RMA method (see Irizarry et al. 2003, Biostatistics 4(2): 249-64, which is incorporated by reference at least for the methods and compositions described therein) and downstream analysis performed using Bioconductor and R (see Gentleman et al. 2004, Genome Biol. 5(10): R80, which is incorporated by reference at least for the methods described therein). Initial quality control was performed and included measurements of RNA degradation and signal distribution. One sample was removed from further analysis after identification as an outlier following principle component and hierarchical clustering analysis. Genes defined as specifically expressed by PDGFαR$^+$ cells were greater than 3 fold expressed and significant using a moderated t-test statistic with 5% false discovery rate cut-off (q<0.05, n=5; linear modeling empirical Bayes test statistic) (see Smyth 2004, Stat. Appl. Gener. Mol. Bio. 3: Article 3, which is incorporated by reference at least for the methods and compositions described therein). The differentially expressed genes were further filtered to remove genes highly expressed by human microglial cells (CD11b-defined, n=3), relative to adult A2B5-sorted WMPCs. Gene ontology and Ingenuity Pathway Analysis (Ingenuity Systems, Redwood City, Calif.) were performed on the list of PDGFαR specific genes. Gene ontology over-representation was performed using NIH DAVID (see Dennis et al. 2003, Genome Biol 4(5): P3, which is incorporated by reference at least for the methods described therein). Significance p-values calculated in Ingenuity (Ingenuity Systems, Redwood City, Calif.) were based on a right-tailed Fisher's Exact test to identify over-represented functional/pathway annotations, that is annotations which have more differentially expressed genes than expected by chance. Individual networks of genes were selected according to relevance score and composition of gene constituents. Gene set enrichment analysis was performed using the PGSEA package and significance assessed by fitting the relative enrichment of individual pathways to a linear model and using a moderated t-test statistic to assign significance. The resulting p-values were corrected for multiple testing correction using the false discovery rate.

Results

CD140a Defines a Population of Olig2+ Glial Progenitor Cells:

In the human forebrain, glial progenitor cells (GPCs) are most actively generated during the latter part of the second trimester. To assess the geographic distribution of CD140a/PDGFαR$^+$ cells in the late second trimester human forebrain, sections of 22 week g.a. forebrain were immunolabeled with a monoclonal anti-CD140a IgG, that recognizes an epitope within the PDGFαR ectodomain (see LaRochelle et al. 1993, Cell Growth Differ. 4(7): 547-53, which is incorporated by reference at least for the methods and compositions described therein) Immunostaining revealed that CD140a$^+$ cells pervaded the developing human forebrain, extending through the intermediate zone to the developing cortical mantle, with a morphology similar to that of NG2-defined adult human OPCs.

Photomicrographs showed that CD140a/PDGFαR expressing cells were found in the developing cortical mantle of 22 wk gestational age fetal brain. All identifiable CD140a-positive cell bodies co-expressed the oligodendrocyte lineage transcription factor Olig2. Consistent with a neural progenitor phenotype, CD140a$^+$/PDGFαR$^+$ cells within the intermediate zone co-expressed the progenitor-expressed transcription factor Sox2. Confocal microscopy determined that a proportion of PDGFαR$^+$/CD140a$^+$ cells labeled with anti-Ki67 antibody, a marker of cells in active cell cycle.

Virtually all CD140a$^+$ cells co-labeled with the oligodendrocyte lineage transcription factor olig2, while sox2 was co-expressed by a fraction of them. A significant proportion of CD140a$^+$ cells expressed Ki67, a marker of actively cycling cells. In contrast, no co-localization was noted with either GFAP, an astrocyte marker, or HuD, a marker of committed neurons. Together, these data demonstrate that CD140a$^+$ cell comprise a population of uncommitted glial progenitors.

Figure 3:
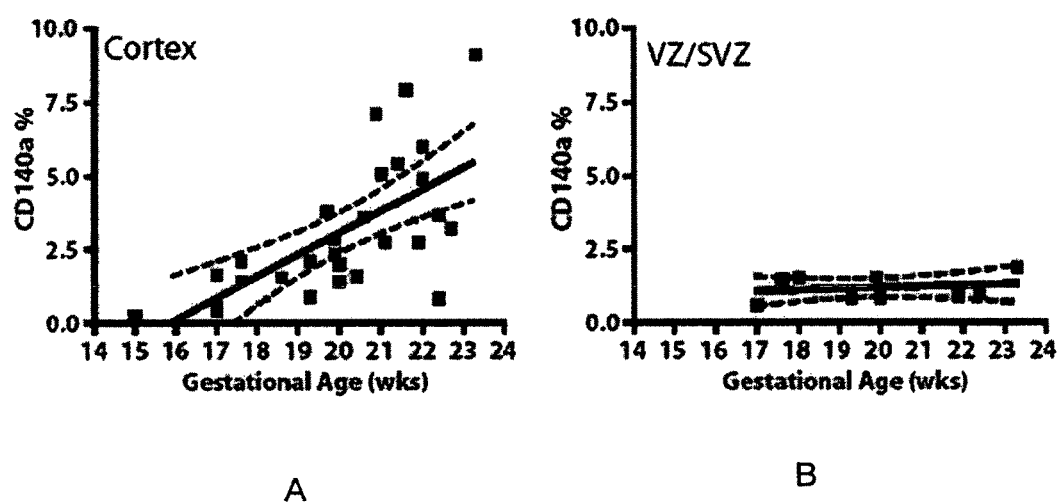
FIGS. 3A and B are graphs showing the relative abundance of PDGFαR cells in the fetal germinal zones and overlying intermediate zone and cortex. CD140a+ cells were rare in early second trimester cortex/IZ and gradually increased with gestational age (n=29) (FIG. 3A). In contrast, the relative incidence of CD140a cells remained relatively constant during the second trimester in dissected germinal zones (VZ/SVZ) (n=10) (FIG. 3B).

CD140a$^+$ GPCs Appeared and Accumulated During Second Trimester Cortical Expansion:

Flow cytometry revealed an abundant population of CD140a$^+$/PDGFαR$^+$ GPCs at 20-22 weeks gestation, by which point 4.8±0.7% of cells within cortical dissociates, which included admixed intermediate zone and cortical mantle, were sorted as CD140a$^+$ (n=13, standard error [SE]). Flow cytometry was used to determine the relative abundance of PDGFαR cells in the fetal germinal zones and overlying intermediate zone and cortex of a 20-22 wk fetal cortex/IZ dissociate. CD140a+ cells were rare in early second trimester cortex/IZ and gradually increased with gestational age (n=29). In contrast, the relative incidence of CD140a cells remained relatively constant during the second trimester in dissected germinal zones (VZ/SVZ) (n=10). At earlier gestational ages (g.a) relatively few CD140a$^+$ cells were noted; appreciable numbers first began to appear at 16 weeks g.a. Over the period of 16-23 weeks, encompassing the latter half of second trimester development, a significant correlation between the incidence of cortical CD140a$^+$ cells and gestational age (p<0.0001, r$^2$=0.43, df=26) was noted. In contrast, the relative incidence of CD140a$^+$ cells within the dissected ventricular and subventricular zones did not increase with gestational age (p=0.57, r$^2$=0.04, df=10) (FIG. 3A). The relatively constant proportion of CD140a$^+$ cells in the VZ/SVZ, in contrast to the rapidly increasing proportion of CD140a$^+$ cells in the presumptive white matter and cortex (3.1±0.4 vs. 1.2±0.1%; unpaired t-test, p=0.012, df=37), demonstrate a monotonic colonization of the developing brain by newly generated VZ/SVZ-derived GPCs (FIG. 3B).

CD140a$^+$/PDGFαR$^+$ Cells Comprise a Subpopulation of A2B5$^+$ Glial Progenitor Cells:

A2B5$^+$/PSA-NCAM$^-$ cells derived from the fetal human brain comprise a phenotypically heterogeneous cell population. Although they include a myelinogenic fraction of bipotential GPCs, they also include glial cells that appear restricted to astrocyte phenotype, typically co-expressing GFAP and A2B5 immunoreactivities. Dissociated fetal cells were depleted of PSA-NCAM$^+$ cells by immunomagnetic sorting, and then subjected to two-color flow cytometry for A2B5 and CD140a.

Figure 4:
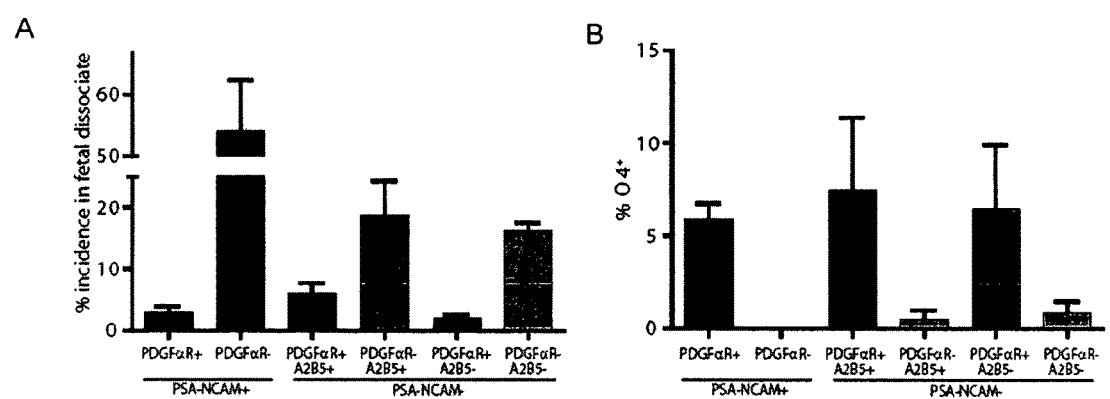
FIGS. 4A and B are graphs showing CD140a/A2B5/PSA-NCAM cytometry data from fetal dissociates.

Fetal dissociates were immunomagnetically selected on the basis of PSA-NCAM antigenicity. PSA-NCAM cells were then subject to two-color FACS/cytometry for CD140a and A2B5 using PE and APC conjugated antibodies respectively. Positive selection gates were defined using fluorescence-minus one (FMO) controls by substitution of either A2B5 or CD140a antibodies with a matched isotype control conjugated antibody. A2B5 and C140a-specific antibodies were also combined. A large proportion of CD140a-labelled cells co-expressed A2B5. PSA-NCAM+ cells underwent single color CD140a cytometry/FACS. FIG. 4A, shows the relative fractions of all six sub-fractions calculated from the combined MACS and FACS procedure (n=4, 19-22 wk gestational age). Each sort was then plated in T3/0.5% pd-FBS containing media for 7 days then stained and counted for the oligodendrocyte antigen O4 (FIG. 4B). Each CD140a+ fraction regardless of A2B5 or PSA-NCAM status gave rise to a higher proportion of O4+ oligodendrocytes (n=3 samples).

CD140a$^+$/PDGFαR$^+$ cells were significantly more abundant, by 2.6-fold, in the A2B5$^+$/PSA-NCAM$^-$ pool than in the overall population from which both derived (23.2±3% in A2B5$^+$/PSA-NCAM$^-$ vs. 10.9±3%; t-test p=0.0324, n=4) (FIG. 4A). Among the CD140a$^+$/PDGFαR$^+$ GPCs, 70±10% co-expressed A2B5$^+$ when analyzed within 48 hrs of tissue dissociation (n=4). Post-sort analysis of oligodendrocytic potential was assessed in 1% platelet-depleted serum (PD-FBS) and triiodothyronine (T3) supplemented media. After 7 days, matched cultures were immunostained using mAb O4, which recognizes immature postmitotic oligodendrocytes in the human (see Armstrong et al. 1992, J. Neurosci 12(4): 1538-47; Kirschenbaum et al. 1994, Cerebral Cortex 4(6): 576-89 and Roy et al. 1999, J. Neurosci. 19(22): 9986-95, which are incorporated by reference at least for the methods and compositions described therein). Although oligodendrocyte differentiation was limited by the presence of 1% PD-FBS, the proportion of O4$^+$ oligodendrocytes was substantially greater in all CD140a$^+$ cell fractions than in their matched CD140a$^-$ counterparts (n=3 sorts) (FIG. 4A).

Two-color FACS performed without antecedent PSA-NCAM depletion revealed that among A2B5$^+$ cells—which by virtue of including neurons and immature astrocytes, comprised 38.1±4.9% of all dissociated forebrain cells (18-23 wks g.a., n=11)–5.3±1.5% expressed PDGFαR, compared with 4.0±1.4% PDGFαR$^+$ within the entire dissociate (n=3, two-color sorts). Thus, CD140a$^+$ cells comprise a distinct, relatively small subpopulation of A2B5$^+$ glial progenitor cells.

Oligodendrocyte Generation was Restricted to CD140a$^+$ Cells:

Fluorescence-activated cell sorting (FACS) was used to separately isolate CD140a$^+$ and CD140$^-$ cells Immediately after sorting, the CD140a$^+$ cells were found to be uniform in size, relatively small and phase bright. Within 24 hrs, most were observed to elaborate fine processes, initially as bipolar cells.

Photomicrographs showed that CD140a sorted cells express markers of GPCs. The phenotype of CD140a-sorted cells was assessed using immunocytochemistry at 24 hrs post-sort. At this stage, CD140a$^+$/PDGFαR$^+$ sorted cells uniformly expressed CD140a/PDGFαR immunoreactivity. At high power, CD140a$^+$ expressing cells co-expressed transcription factor markers of oligodendrocyte lineage, Olig2 and neural progenitors, Sox2. CD140a$^-$ depleted cells did not express CD140a immunoreactivity. Most CD140a/PDGFαR-depleted cells were neuronal lineage expressing βIII-tubulin and HuD. A smaller subset of depleted cells consisted of GFAP/AQP double-labeled astrocytes.

The CD140a$^+$ cells uniformly expressed CD140a/PDGFαR, and co-expressed the transcription factors olig2 and sox2, which are both expressed by uncommitted glial progenitors. In contrast, the CD140a⁻ fraction was largely devoid of olig2⁺ cells, as well as of CD140a⁺/PDGFαR⁺ cells.

Figure 5:
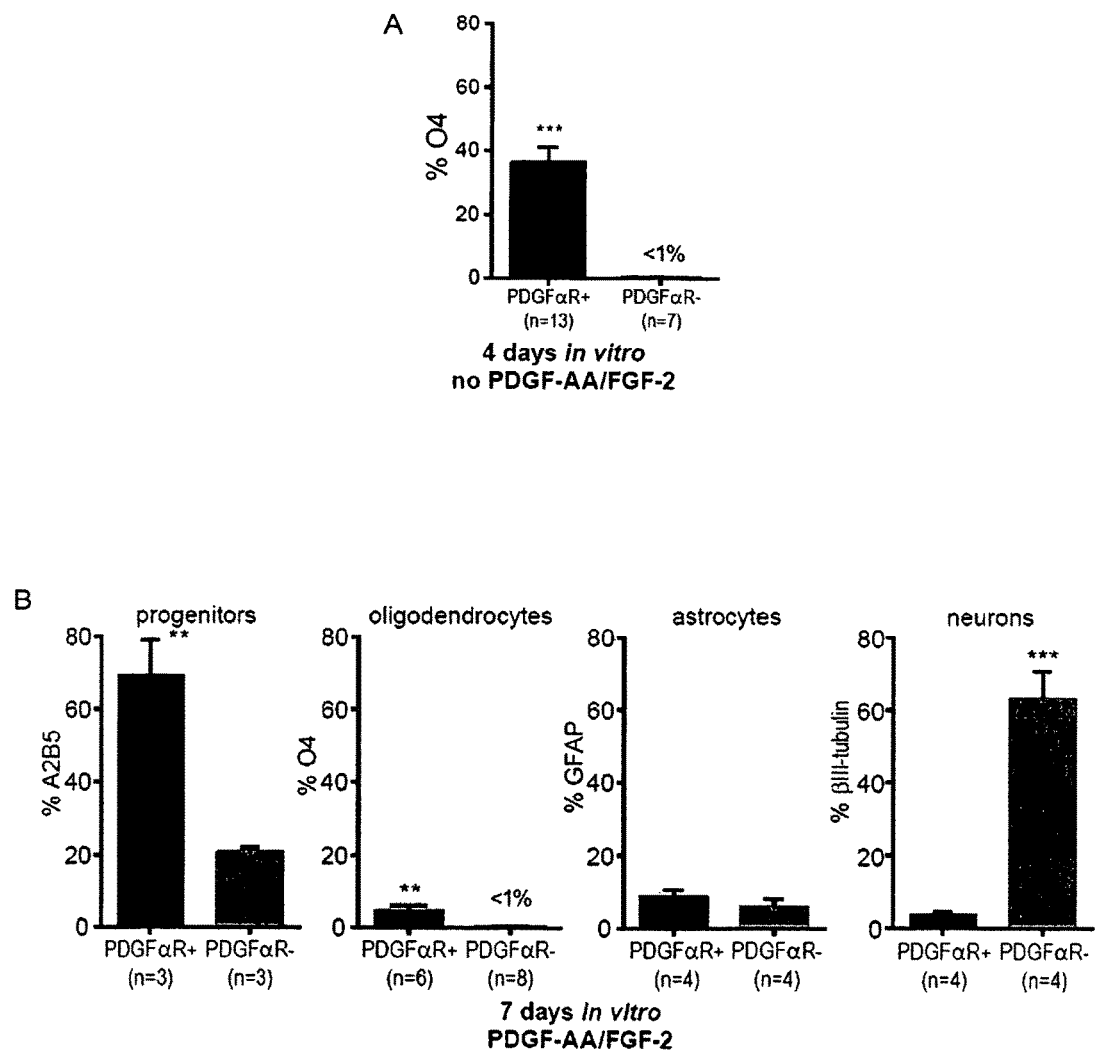
FIGS. 5A and B are graphs showing that CD140a-sorted cells mature primarily as oligodendrocytes and can be maintained as progenitors in PDGF-AA/FGF2.
As shown in FIG. 5B, CD140a-sorted cells were cultured for 7 days in the presence of PDGF-AA and FGF-2 (each 20 ng/ml) and stained for phenotypic markers of neural cell lineages. In this condition, CD140a$^+$ cells were maintained as A2B5-expressing progenitor cells and spontaneous oligodendrocyte differentiation was inhibited, the proportion of O4$^+$ oligodendrocytes was reduced to less than 10%. In contrast, CD140a$^-$ cells were primarily composed of βIII tubulin$^+$ neurons.

In order to encourage oligodendrocytic differentiation, the two populations were then each raised with T3 in the absence of growth factors. Within 1-2 days, most CD140a⁺ cells exhibited a progenitor-like morphology being typically bipolar with small compact cell bodies and expressed nuclear-localized Olig2 protein. As shown in FIG. 5A, after 4 days, it was found that 36.6±5% of CD140a-sorted cells expressed oligodendrocyte marker O4 (n=13), whereas only 0.1% of CD140a⁻ cells expressed O4 at this point (n=7, one sample had approximately 1% O4+ cells, while none could be identified in the remaining 6). As shown in FIG. 5B, at 7 days the vast majority of CD140a⁻ cells could be identified as either as TuJ1⁺ neurons (63±8%, n=4 fetal samples), or as GFAP⁺ astrocytes (6±2%, n=4). A subset of persistent A2B5⁺ cells (21±1%, n=3), some of which co-expressed GFAP, was also noted in the CD140a⁻ cultures. Moreover, exposure to serum concentrations of up to 10%, with or without supplementation by 20 ng/ml IGF1, did not trigger the appearance of O4⁺ oligodendrocytes in CD140a⁻ cultures. Overall then, a >200-fold increase in the percentage of O4⁺ cells in the CD140a⁺ fractions was noted, relative to their CD140a⁻ remainders (37% CD140a⁺ vs. 0.14% CD140a⁻, p<0.0001, two-tailed t-test; df=18). Thus, in these dissociates of second trimester fetal human forebrain, O4⁺ oligodendrocytes were produced only by CD140a⁺ progenitor cells.

CD140a⁺ Cells can be Instructed to Generate Both Oligodendrocytes and Astrocytes:

FACS-sorted CD140a⁺ cells were cultured in the absence of growth factors. By 7 days, although some oligodendrocytic death was found, surviving oligodendrocytes were noted to express the mature oligodendrocyte marker O1 and to have developed the complex branching morphology of maturing oligodendroglia. Yet, whereas such oligodendrocytic differentiation from CD140a⁺ cells could be promoted by T3 and mitogen removal in serum-free media, astrocytic differentiation could also be readily induced, using serum and/or BMP exposure. It was found that addition of either serum or BMP-4 immediately after sort induced rapid GFAP⁺ astrocytic differentiation. In cultures exposed to 0.5% plasma derived (PD)-FBS, by 7 days post sort there was a 3.5-fold induction of astrocytic phenotype from 8.8% to 30.7% (p=0.0023, unpaired t-test, df=5). Similarly BMP-4 addition rapidly induced a dose-dependent increase in GFAP⁺ astrocytes, from 8% to >40% after exposure to 50 ng/ml BMP-4 for 4 days (p<0.01; F=12.4; by one-way ANOVA with Dunnett's post hoc analysis). In contrast, oligodendrocyte lineage differentiation was dramatically inhibited by BMP-4 treatment, such that the incidence of O4⁺ cells fell from >30% to <5% at 4 days in vitro (p<0.01; F=12.7; ANOVA with Dunnett's post hoc). As a result, the GFAP/O4 ratio in these cultures increased in response to BMP-4, from less <0.5 to more than 15. Post hoc analysis showed 5 ng/ml BMP-4 induced significant changes in proportions of GFAP⁺ and O4⁺ cells (p<0.05). CD140a⁺ cells could be maintained as bipotential progenitors in vitro. The appearance of O4⁺ oligodendrocytes at 4 days was almost completely blocked by the addition of the mitogens PDGF-AA and FGF-2, both at 20 ng/ml. In matched cultures, only 2.4±1.2% of CD140a⁺ cells developed as oligodendrocytes by day 4 in the presence of mitogens (n=5). The vast majority of these cells remained as A2B5⁺ progenitors (75±7%, n=3), and could be maintained as such for at least a week in vitro; only 4.8±1.2% were O4+ at 7 days, while >70% remained A2B5⁺ at one week (n=6). In addition, the gradual appearance of flat-appearing GFAP⁺ astrocytes (8.8±1.9%, n=4) was noted. Withdrawal of FGF and addition of T3 to the PDGF-supplemented media induced partial oligodendrocyte differentiation, increasing the incidence of O4+ cells by almost 3-fold to 13.7±2.9% (p=0.0123, t-test, n=3); nonetheless, the majority of cells still remained as A2B5⁺ progenitors (59.3±13.7%, p<0.05, paired t-test, n=4).

To examine the effect of tonic BMP signaling on fetal CD140a⁺ cells, an attempt was made to block astrocyte lineage commitment with noggin, a broad-spectrum BMP antagonist whose treatment maintains adult GPCs as A2B5⁺ progenitors. When added to CD140a⁺ cultures in the absence of growth factors for 4 days, 100 ng/ml noggin potently inhibited BMP-4 induced astrocytic differentiation (p<0.05, Tukey's post hoc test). Noggin addition reversed the inhibitory effect of BMP-4 on oligodendrocyte commitment, such that the percentage of O4⁺ cells returned to null control levels (21.0±3% O4+ cells in BMP-4+noggin, vs. 4.3±1% O4⁺ cells in BMP-4 alone; p<0.05). Baseline levels of astrocytic and oligodendrocytic differentiation were unaffected by noggin treatment in the absence of exogenous BMP ligands (8.1±3% and 8.1±4% GFAP⁺ in the null and 100 ng/ml noggin treated groups, respectively; 22.6±4% and 21.0±3% O4⁺ cells in null and 100 ng/ml noggin treated groups).

CD140a⁺ GPCs Myelinated the Hypomyelinated Shiverer Mouse Brain Upon Xenograft:

A cohort of 7 myelin-deficient shiverer$^{shi/shi}$ mice were transplanted with 5×10⁴ cells each of CD140a-sorted GPCs. The xenografts were delivered neonatally, as intracallosal injections, as previously described (see Windrem et al. 2004, Nat. Med. 10(1):93-97, which is incorporated by reference at least for the methods and compositions described therein). Under these conditions, A2B5⁺/PSA-NCAM⁻ sorted fetal human GPCs typically begin to generate myelin by 8 weeks after neonatal transplant, myelinating relatively large volumes of otherwise hypomyelinated white matter by 12 weeks. To assess the relative competence of CD140a-sorted cells to effect myelin production and axonal ensheathment, the CD140a-engrafted shiverers were sacrificed at 8-12 weeks of age, and their brains cryosectioned and immunostained for myelin basic protein (MBP), which is not otherwise expressed in shiverer. The CD140a-engrafted mice indeed exhibited significant and widespread myelination of the callosum, capsules and fimbria, in a geographic pattern similar to that which had been previously observed using A2B5-sorted GPCs.

Figure 6:
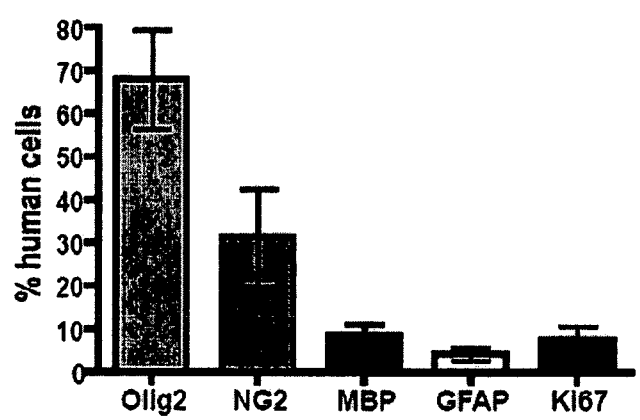
FIG. 6 is a graph showing quantification of human CD140a$^+$/PDGFαR$^+$ cell fate at 8-12 weeks post implantation (n=3) into the hypomyelinated forebrain of neonatal shiverer mice.

Human fetal CD140a⁺/PDGFαR⁺ GPCs were transplanted into the hypomyelinated forebrain of neonatal shiverer mice. At 8-12 weeks post injection, a fraction of human cells recognized by anti-human nuclear antigen (hNA) differentiated into myelinating oligodendrocytes expressing the myelin protein gene MBP. Consistent with the time course of human myelination, a large proportion of transplanted cells remained as NG2-expressing GPCs at 8-12 weeks post implantation. However, only a small fraction of human cells differentiated as astrocytes labeled with GFAP. FIG. 6 shows the quantification of human cell fate at 8-12 weeks post implantation (n=3).

Quantification within the fimbria revealed that the majority of human cells were of oligodendrocytic lineage, with 68±14% of human nuclear antigen (hNA)-defined human cells co-expressing the early glial and oligodendroglial transcription factor Olig2 (n=3 brains scored). By 8 weeks after injection, a timepoint at which myelinogenesis from implanted A2B5-defined fetal GPCs is just beginning, 8±3% of human CD140-sorted cells had already differentiated as MBP+ oligodendrocytes (n=3, FIG. 6). At that relatively early timepoint, a third persisted as NG2+ GPCs (31±14%, n=3; FIG. 6); a fraction of these remained mitotically competent, as defined by Ki67 expression (8±4%, n=3; FIG. 6). Strikingly though, less than 5% of implanted human CD140a+ cells differentiated as GFAP-defined astrocytes (FIG. 6). These findings indicate that CD140a+ fetal human GPCs, like the larger pool of A2B5+/PSA-NCAM− GPCs of which they are a part, can effect rapid oligodendrocytic maturation and myelinogenesis in vivo.

CD140a+ Cells Express a Transcript Profile of Uncommitted Glial Progenitor Cells:

To better assess the differentiation state of CD140a-sorted human GPCs, their expression profiles, relative to CD140a− fetal cortical cells were assessed. Taqman® (Roche, Alameda, Calif.) low density microfluidic arrays were used to achieve high throughput quantitative RT-PCR (qPCR) of a panel of 48 marker genes, that were identified as potentially predictive of glial progenitor cell fate (Table 3).

TABLE 3

Marker Gene expression profile of CD140a+/PDGFαR+ fetal human oligodendrocyte progenitor cells.

| Cell Type | Symbol (Name) | qPCR ratio |
|---|---|---|
| Oligodendrocyte Progenitor | CSPG4 (NG2) | 47.95 (14.73-156.04) |
| | PDGFRA | 524.65 (175.68-1,566.81; q = 0.021) |
| | PTPRZ1 (RPTPzeta) | 3.74 (2.81-4.99; q = 0.034) |
| | GD3 synthase | 1.43 (0.91-2.23) |
| Oligodendrocyte lineage | CNP | 4.89 (3.83-6.24; q = 0.020) |
| | Nkx2.2 | 42.83 (17.36-105.66; q = 0.042) |
| | Olig1 | 54.79 (28.14-106.67; q = 0.021) |
| | Olig2 | 196.05 (92.19-416.91; q = 0.020) |
| | SOX10 | 578.59 (247.93-1,350.21; q = 0.020) |
| Myelinating oligodendrocyte | CLDN11 (claudin 11/OTP) | 16.64 (8.27-33.47; q = 0.042) |
| | GALC | 1.06 (0.87-1.29) |
| | MBP | 1.25 (0.22-7.20) |
| | MOBP | 0.52 (0.11-2.47) |
| | MOG | 0.10 (0.04-0.25) |
| | NKX6.2 (Gtx) | 6.29 (1.71-23.08) |
| | PLP1 (PLP/DM20) | 1.30 (0.78-2.16) |
| Astrocyte | AQP4 | 0.79 (0.59-1.07) |
| | GFAP | 3.83 (1.94-7.56) |
| | GLUL (glutamine synthase) | 4.94 (2.28-10.71) |
| | S100B | 69.52 (23.10-209.17; q = 0.046) |
| | SLC1A2 (GLT-1) | 1.09 (0.99-1.20) |
| | TNC (tenascin C) | 2.12 (1.58-2.85) |
| | CD44 | 2.89 (2.07-4.05) |
| Radial Glia | FABP7 (BLBP) | 1.58 (1.30-1.93) |
| | SLC1A3 (GLAST) | 2.53 (1.88-3.41) |
| Neural progenitor and stem cell | ASCL1 (MASH1) | 1.68 (1.12-2.50) |
| | DCX (doublecortin) | 0.28 (0.20-0.39; q = 0.046) |
| | SOX1 | 0.64 (0.38-1.09) |
| | HES1 | 3.40 (1.88-6.13) |
| | MSI1 | 0.37 (0.28-0.48; q = 0.046) |
| | NES | 2.23 (1.64-3.04) |
| | NR2E1 (tailless) | 0.43 (0.23-0.83) |
| | SOX2 | 4.52 (2.96-6.88; q = 0.046) |
| Neuron | MAP2 | 1.20 (0.88-1.64) |
| | NEFH | 0.42 (0.29-0.61) |
| | TUBA1A (T alpha 1) | 0.37 (0.29-0.49; q = 0.046) |
| | TUBB3 (βIII-tubulin) | 0.31 (0.23-0.41; q = 0.042) |
| | ELAVL3 (HuC) | 0.51 (0.37-0.70) |
| | ELAVL4 (HuD) | 0.21 (0.15-0.29; q = 0.034) |
| Endothelial | CDH5 (VE-cadherin) | 0.56 (0.37-0.86) |
| | TEK (TIE2) | 1.90 (1.29-2.80) |
| | VWF | 0.50 (0.11-2.33) |
| Microglia | CD68 | 3.41 (2.41-4.84; q = 0.046) |
| | CD86 | 78.63 (32.96-187.57; q = 0.031) |
| | PTPRC (LCA) | 25.19 (9.05-70.08) |

Fetal cortical dissociates were FACS sorted for CD140a/PDGFαR immunoreactivity and immediately frozen for RNA analysis (n=6 fetal samples). Expression of cell type-specific markers was measured by quantitative Taqman® RT-PCR (Applied Biosystems, Foster City, Calif.) and compared against the matched CD140a−/PDGFαR− pool. Expression data was calculated via normalization to GAPDH, and significance was assessed by paired t-test statistics. P-value were adjusted for multiple testing effects using false discovery rate (q-value). Mean ratio of expression and standard error ranges are shown. Significantly expressed genes at 5% FDR are bolded, significantly depleted genes are italicized. OPC-expressed genes were highly enriched in fetal CD140a/PDGFαR-sorted cells.

Using 6 fetal forebrain samples of 20-22 weeks g.a., FACS was used to sort the cortical dissociates on the basis of CD140a expression, and then the marker gene expression patterns of the CD140a$^+$ and CD140a$^-$ fractions were compared (Table 3). PDGFRA mRNA was >500 fold higher in CD140a$^+$ than CD140a$^-$ cells (paired t-test, p=0.013), validating both the stringency of the sort conditions, and the use of anti-CD140a as a means of isolating the CD140a$^+$/PDGFαR$^+$ population. Significantly higher expression of a number of OPC and oligodendrocyte-lineage markers were also noted. For instance, the CSPG4 proteoglycan NG2 was overexpressed almost 50 fold in CD140a$^+$ cells, and the oligodendrocyte lineage transcription factors Olig1, Olig2, Nkx2.2 and Sox10 were all similarly enriched in CD140a$^+$ cells (Table 3). Indeed, the ratios of expression were extreme in the cases of Olig2 and Sox10—each was expressed over 150-fold more in CD140a$^+$ than CD140$^-$ cells—suggesting an almost complete depletion of olig2/sox10 cells from the CD140a$^-$ population. In addition, the progenitor profile of CD140a$^+$/PDGFαR$^+$ cells was confirmed by their significant expression of Sox2, a neural stem/progenitor expressed transcription factor.

Consistent with a progenitor cell phenotype, mRNAs encoding differentiated cell markers were not enriched in CD140a$^+$ OPCs. Oligodendrocyte-expressed myelin protein genes, MBP, PLP, MOBP, MOG ranged in expression between 0.1 and 1.3-fold in CD140a$^+$ cells. The only exception was oligodendrocyte transmembrane protein (OTP), which was found 6.3 fold higher in CD140a$^+$/PDGFαR$^+$ than CD140a$^-$/PDGFαR$^-$ cells (p=0.033). In agreement with the antigenic phenotyping, astrocyte markers AQP4 and GFAP were not enriched in fetal CD140a-defined OPCs (Table 4).

TABLE 4

GPC-specific and cell-cell signaling genes are highly expressed by fetal CD140a-defined cells.

| | Symbol | Description | GeneID | Ratio | q-value |
|---|---|---|---|---|---|
| Cell type specific marker | PDGFRA | platelet-derived growth factor receptor, alpha | 5156 | 30.8 | 3.26E−10 |
| | OLIG1 | oligodendrocyte transcription factor 1 | 116448 | 55.52 | 3.46E−11 |
| | OLIG2 | oligodendrocyte lineage transcription factor 2 | 10215 | 24.15 | 9.93E−11 |
| | NKX2-2 | NK2 transcription factor related, locus 2 | 4821 | 19.74 | 2.86E−09 |
| | SOX10 | SRY (sex determining region Y)-box 10 | 6663 | 31.08 | 7.80E−12 |
| | CSPG4 | NG2 | 1464 | 11.11 | 2.19E−09 |
| | ST8SIA1 | GD3 synthase | 6489 | 3.25 | 1.28E−06 |
| | S100B | S100 beta | 6285 | 25.56 | 2.32E−12 |
| | CLDN11 | oligodendrocyte transmembrane protein, claudin11 | 5010 | 4.01 | 2.59E−03 |
| | CNP | CNPase | 1267 | 3.1 | 7.63E−08 |
| Chondroitin enzymes | CSGALNACT1 | chondroitin sulfate N-acetylgalactosaminyl-transferase 1 | 55790 | 13.01 | 6.52E−07 |
| | UST | uronyl-2-sulfotransferase | 10090 | 7.52 | 3.39E−06 |
| | CHST11 | carbohydrate (chondroitin 4) sulfotransferase 11 | 50515 | 5.78 | 1.61E−08 |
| | B3GAT2 | beta-1,3-glucuronyltransferase 2 | 135152 | 4.37 | 1.60E−04 |
| | HS3ST3A1 | heparan sulfate 3-O-sulfotransferase 3A1 | 9955 | 4.29 | 1.99E−03 |
| | CHST3 | carbohydrate (chondroitin 6) sulfotransferase 3 | 9469 | 3.68 | 2.83E−05 |
| | XYLT1 | xylosyltransferase I | 64131 | 3.06 | 8.44E−07 |
| | BCAN | brevican | 63827 | 6.02 | 1.80E−06 |
| | CSPG4 | NG2 | 1464 | 11.11 | 2.19E−09 |
| | CSPG5 | neuroglycan C/NGC | 10675 | 5.71 | 1.31E−07 |
| | PTN | pleiotrophin; HB-GAM | 5764 | 3.65 | 1.65E−04 |
| Wnt related | TCF7L1 | TCF3 | 83439 | 4.66 | 4.04E−07 |
| | TCF7L2 | TCF4 | 6934 | 3.09 | 2.64E−07 |
| | PPAP2B | phosphatidic acid phosphatase type 2B | 8613 | 4.58 | 3.29E−05 |
| | CCND1 | cyclin D1 (PRAD1: parathyroid adenomatosis 1) | 595 | 13.18 | 2.82E−09 |
| Notch related | CNTN1 | contactin 1 | 1272 | 30.41 | 4.01E−15 |
| | JAG1 | jagged 1 | 182 | 3.31 | 5.76E−05 |
| | MAML2 | mastermind-like 2 (Drosophila) | 84441 | 8.41 | 1.86E−08 |
| | HEY2 | hairy/enhancer-of-split related with YRPW motif 2 | 23493 | 4.49 | 1.35E−03 |
| EGFR related | EGFR | epidermal growth factor receptor | 1956 | 3.3 | 6.63E−03 |
| | ERBB3 | EGFR-related receptor, HER3 | 2065 | 9.74 | 1.59E−06 |

TABLE 4-continued

GPC-specific and cell-cell signaling genes are
highly expressed by fetal CD140a-defined cells.

| Symbol | Description | GeneID | Ratio | q-value |
|---|---|---|---|---|
| GRB14 | growth factor receptor-bound protein 14 | 2888 | 4.99 | 1.62E−02 |
| TGFA | transforming GF, alpha; TGF-alpha | 7039 | 5.49 | 4.35E−06 |
| CD9 | CD9 antigen (p24) | 928 | 7.44 | 1.10E−03 |

The microarray profiles of CD140a-sorted cells were compared directly to their depleted controls. CD140a enriched genes were defined as those genes greater than 3 fold higher expressed in sorted cells and significant following paired t-tests using a moderated t-test statistic and 5% false discovery rate cut-off. Using these criteria 408 genes were identified as expressed by CD140a$^+$ GPCs. Selected genes on the basis of cell type expression or signaling pathway membership are shown.

In contrast, the pro-glial calcium buffer S100β was significantly upregulated in CD140a$^+$ cells, 17.2-fold higher in CD140a$^+$ than CD140a$^-$ cells (p=0.003). Finally, transcripts expressed by neurons were significantly depleted from CD140a$^+$/PDGFαR$^+$ cells, tubulin α1 and βIII-tubulin were 3.3 and 4.0 fold higher in CD140a$^-$ than CD140a$^+$ cells.

Relatively high expression of the microglial selected transcripts CD68 and CD86 were noted. However, antigenically defined human OPCs may share surface antigens with microglial cells as fetal ganglionic eminence NG2$^+$ cells can express CD68 and tomato-lectin$^+$ cells can similarly express PDGFαR, indicating native expression of microglial markers by migrating CD140a$^+$/PDGFαR$^+$ glial progenitors.

Using Affymetrix (Santa Clara, Calif.) HG-U133+2 arrays, the transcription profile of fetal CD140a enriched and depleted cells were analyzed. Individual CD140a-sorted samples were compared to their matched depleted remainders, and differential gene expression analysis performed. Enriched genes were defined as those greater than 3-fold over-expressed in CD140a$^+$ mRNAs relative to the depleted pool. Genes were defined as significantly enriched using a moderated t-test statistic with 5% false discovery rate cut-off, via linear modeling employing an empirical Bayes test statistic (see Smyth 2004, Stat. Appl. Genet. Mol. Bio. 3: Article 3, which is incorporated by reference at least for methods and compositions described therein). Following annotation, 408 genes were identified as both significantly regulated and selectively overexpressed by at least 3-fold by CD140a$^+$/PDGFαR$^+$ cells. In accord with the qPCR marker data, the CD140a-sorted cells expressed significantly high levels of the prototypic GPC markers OLIG1 (56 fold higher in PDGFαR$^+$), OLIG2 (24-fold), NKX2.2 (20-fold), PDGFRA (31-fold), SOX10 (31-fold), CSPG4/NG2 (11-fold) and ST8SIA1, the synthetic enzyme for A2B5 antigen (3.3-fold). The high expression of PDGFRA, NG2, and ST8SIA1/SIAT8A resembled the phenotype of adult human GPCs. Similarly, S100β, OTP and CNP were also significantly up-regulated in CD140a-sorted cells (Table 4). Markers of other neural phenotypes, including oligodendrocytes, astrocytes, neurons and neural stem cells were not highly expressed by CD140a$^+$ cells. Thus, all 10 of the marker genes identified as significantly over-expressed by CD140a$^+$ cells in the arrays were additionally validated by real-time qPCR, suggesting the fidelity with which the microarray data reflects the genomic profile of human CD140a$^+$/PDGFαR$^+$ GPCs.

Gene Expression Pattern of CD140a$^+$ GPCs Indicates Prominent Glycan-Regulated Signaling:

To identify those signaling pathways that regulate the specification and differentiation of human CD140a$^+$ cells, a literature-based data mining and pathway analysis was performed, concentrating first on the functional classification and over-representation of gene ontology (GO) annotations. It was noted that genes involved in nervous system development were especially prevalent (Benjamini corrected p-value=8.6×10$^{-5}$; GO Biological process GO:0007399). In addition, a cluster of ontologies were identified involved in cell communication, signal transduction and cell surface receptor linked signal transduction (Enrichment Score: 4.36, GO biological process annotations). A large number of glycoproteins (Swiss-Prot; Benjamini corrected p-value=1.8×10$^{-14}$) and integral plasma membrane proteins (p=1.4×10$^{-5}$, GO:0005887) were identified. Ingenuity Pathway analysis (IPA) was performed, which indicated the differential representation of genes involved in neurogenesis (p=1.6×10$^{-8}$) and, interestingly, schizophrenia (p=5.0×10$^{-12}$).

KEGG-based gene set enrichment analysis identified 37 pathways whose regulation was significantly different in CD140a$^+$ than CD140a$^-$ cells (q<0.05). Among these, the most significant were 'chondroitin sulfate biosynthesis' (q=4.65×10$^{-11}$) and 'glycan biosynthesis 1' (q=1.00×10$^{-8}$). Similarly, Ingenuity (Ingenuity Systems, Redwood, Calif.) identified active synthesis of chondroitin sulfate glycosaminoglycans (GAGs) as the most significant pathway (p=1.32×10$^{-5}$). These biosynthetic pathways largely comprised enzymes involved in CSPG and glycan biosynthesis (Table 4). Among the CD140a-selective transcripts were the chondroitin sulfotransferases, CHST3, CHST11, and uronyl-2-sulfotransferase (UST). In addition, the chondroitin sulphate proteoglycan (CSPG) core proteins themselves were also highly expressed. CSPG4 (NG2) and CSPG5 (neuroglycan) were both expressed at levels 5 fold higher than observed in depleted cells.

Figure 7:
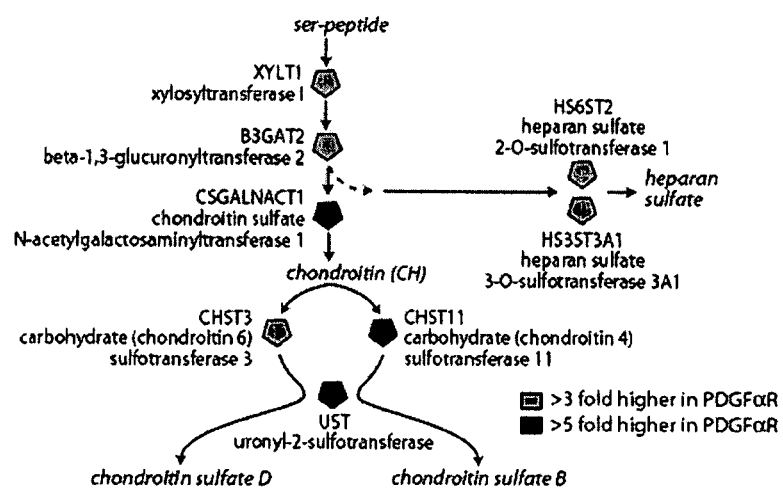
FIG. 7 is a schematic diagram showing that CD140a/PDGFαR sorted cells actively produce chondroitin sulfate B and D moieties.

The predominance of sulfotransferases indicates that the chondroitin produced by CD140a$^+$ cells likely undergoes sulfation to produce chondroitin sulfate B and D moieties (CS-B and CS-D) (FIG. 7). CS-GAGs chains can bind many growth factors and act to present them to cell surface receptors; CS-B binds FGF2 and pleiotrophin (PTN), and promotes the mitotic effects of FGF2 on neural progenitors in culture. In this regard, it was noted that PTN mRNA was highly and significantly expressed by PDGFαR cells (3.7 fold, FDR corrected q-value=1.65×10$^{-4}$). Of note, adult human GPCs highly express the PTN-receptor, RTPβ/ζ (PTPRZ1). It was found that fetal CD140a$^+$ cells also over-expressed PTPRZ1, which was significantly enriched by array (moderated t-test, p=0.0085) qPCR confirmed that PTPRZ1 was differentially up regulated in CD140a$^+$ GPCs by 3.74-fold relative to CD140$^-$ cells (q=0.034). This indicates the presence of the PTN/PTPRZ1 autocrine pathway in fetal OPCs as well as adult OPCs, and further indicates prominent CSPG-B-dependent autocrine signaling by PTN.

Transcriptional Profile of CD140a$^+$ GPCs Predicts Active Wnt, Notch, and EGF Pathways:

Gene ontology-based GSEA identified the wnt, notch, and EGF signaling pathways as significantly over-represented in CD140a-sorted cells (q=1.67×10$^{-3}$, 5.06×10$^{-5}$, and 9.26×10$^{-5}$, respectively). Active wnt signaling was indicated by the presence of high levels of two TCF transcription factor isoforms, TCF7L1 and TCF7L2 (Table 4). Furthermore, GSEA of wnt target genes indicated a significant over expression of a number of WNT target genes by CD140a$^+$ cells (p=0.011).

A heatmap was used to show WNT target genes. To investigate the functional significance of wnt signaling pathway relative enrichment in CD140a-sorted cells, Gene Set Enrichment Analysis (GSEA) was performed using annotated wnt target genes. Parametric-GSEA indicated a significant enrichment of wnt target genes in CD140a+ cells (p=0.011). Among those, 15 genes were significantly differentially expressed by CD140a+ and CD140a− cells (>3 fold change, 5% FDR). The resulting heatmap of those genes was plotted for each fetal sample (n=5). The majority 12 of 15 were significantly greater expressed in CD140a-sorted cells.

Wnt target genes included the wnt target gene cyclin D1 (CCND1) which was >13-fold higher in CD140a-sorted cells (Table 4). Together, the expression of these genes suggests active wnt-signaling in PDGFαR$^+$/CD140a$^+$ cells. As PTPZ1 can regulate the tyrosine phosphorylation of β-catenin, the co-regulation of chondroitin-regulated signaling and wnt pathway constituents suggests a common modulation by PTPRZ1.

Four notch regulators were found among the CD140a$^+$ selective genes (p=6.9×10$^{-3}$). These included the notch ligands contactin/F3 (CNTN1) and jagged 1 (JAG1), which can have opposing effects on OPC differentiation in rodents. Contactin was over 30-fold enriched by PDGFαR$^+$ cells (q=4.01×10$^{-15}$), whereas jagged 1 was only 3.3-fold higher. Expression of mastermind-like 2 (MAML2), a coactivator of the notch pathway was also noted, which was 8.4 fold-higher in CD140a-sorted cells (q=1.86×10$^{-8}$). Consistent with notch pathway activation, the HES-related transcription factor HEY2, whose transcription can be activated by notch signaling, was significantly 4.5-fold higher in CD140a$^+$ cells (q=1.35×10$^{-3}$).

A number of tyrosine kinase growth factor receptors and their regulators were similarly overexpressed by fetal CD140a$^+$ GPCs; these included PDGFRA itself, as well as the epidermal growth factor (EGF) family receptors EGFR and erbB3, the expression of which was 3.3- and 9.7-fold higher, respectively, in CD140a$^+$ than CD140a$^-$ cells. The SH3-adaptor protein GRB14, which interacts with the intracellular domains of both the EGFR and PDGFRA receptors, was also significantly overexpressed. In addition, autocrine signaling through EGFR was indicated by high expression of the EGF-ligand TGFα, 5.5 fold (q=4.35×10$^{-6}$). Interestingly, membrane bound TGF-α can be primed to activate EGFR via the tetraspanin protein CD9, which was 7.4-fold enriched in CD140a$^+$ cells (q=1.1×10$^{-3}$). CD9 can strongly enhance EGFR activation via binding of transmembrane TGF-α, suggesting a GPC-selective mechanism for CD9-potentiated signaling through EGFR.

Tetraspanin CD9 And PdgfαR Are Co-Expressed In Fetal Human Progenitors:

It was noted that among membrane proteins, the gene encoding CD9 stood out as differentially over-expressed by fetal human CD140a$^+$ cells. On that basis, it was determined whether fetal human GPCs might be independently separable using CD9 ectodomain-directed FACS. Flow cytometry revealed that CD9$^+$ cells comprised 2.75±0.7% of all cells in the fetal intermediate zone and cortical plate (n=5), and were less common in the fetal VZ, comprising less than 1% of cells (0.51±0.1%). Two-color cytometry was then performed to examine the distribution of CD9$^+$ cells among CD140a$^+$ GPCs. The population of CD9$^+$ cells partially overlapped with CD140a, such that half of CD140a$^+$ GPCs expressed CD9 (49.6±5%, n=6); as such, fully 2.6±1.5% of the entire dissociated pool co-expressed CD140a and CD9.

Fetal dissociates were incubated with CD140a and CD9 antibodies for double CD140a/CD9 cytometry. Fluorescence-minus controls utilizing isotype control antibodies were used to set positive sort gates for each antigen. CD140a/CD9 cytometry was performed on six separate fetal samples (18-20 wk gestational age). Approximately half of CD9$^+$ cells co-expressed CD140a, whereas approximately one third of CD140a$^+$ cells expressed CD9. This represented a highly significant overlap and translates to a 14.4±2.3 fold enrichment of CD9 positive cells following CD140a sorting (p=0.0002). These results are consistent with the 7.4 fold higher expression of CD9 mRNA in CD140a cells compared to the depleted population.

Used alone, CD9 based sorting yielded a highly significant, 14-fold enrichment in CD140a$^+$/PDGFαR$^+$ cells relative to their unsorted dissociates (one sample t-test, p=0.00002). These data indicate the use of CD9 as a marker for an antigenically distinct subpopulation of glial progenitors in the fetal human brain, and further indicate the utility of concurrent CD9 and CD140a-directed FACS for isolation of a highly enriched, oligodendrocyte-competent population of human glial progenitor cells.

What is claimed is:

1. A method of isolating a population of human oligodendrocyte-biased glial progenitor cells, comprising the steps of:
   (a) providing a population of human neural cells or neural precursor cells and
   (b) recovering a population of A2B5+ and PSA-NCAM− human oligodendrocyte-biased glial progenitor cells from the provided population of human neural cells or neural precursor cells using only an agent that selectively binds to the CD140a ectodomain epitope of human PDGFαR, wherein the recovered population of cells has a higher percentage of said human oligodendrocyte-biased glial progenitor cells than when said recovering is carried out using antibodies directed against A2B5 and PSA-NCAM.

2. The method of claim 1, wherein the recovering step is performed by FACS or magnetic sorting.

3. The method of claim 1, wherein the agent is an antibody.

4. The method of claim 1, wherein the recovered human oligodendrocyte-biased glial progenitor cells are immortalized.

5. The method of claim 4, wherein the recovered human oligodendrocyte-biased glial progenitor cells express an exogenous nucleic acid encoding a human telomeric extension reverse transcriptase.

6. The method of claim 1, wherein the provided population is derived from human neural tissue.

7. The method of claim 1, wherein the provided population is derived from human multipotent or pluripotent stem cells.

8. The method of claim 7, wherein the human pluripotent stem cells are induced human pluripotent stem cells.

9. The method of claim 1, wherein the provided population is derived from human fetal cells.

10. The method of claim 1, wherein the provided population is derived from human non-fetal cells.

11. The method of claim 1 further comprising:
culturing the recovered human oligodendrocyte-biased glial progenitor cells under conditions effective to form human oligodendrocytes.

12. The method of claim 1, further comprising: culturing the recovered human oligodendrocyte-biased glial progenitor cells under conditions effective to form human astrocytes.

* * * * *

UNITED STATES PATENT AND TRADEMARK OFFICE
CERTIFICATE OF CORRECTION

PATENT NO. : 9,709,553 B2
APPLICATION NO. : 12/990874
DATED : July 18, 2017
INVENTOR(S) : Goldman et al.

Page 1 of 1

It is certified that error appears in the above-identified patent and that said Letters Patent is hereby corrected as shown below:

In the Specification

At Column 1, Lines 15-18, please delete the following:
"This invention was made with government support under Grant No. R01NS039559 awarded by the National Institute of Neurological Disorders and Stroke. The government has certain rights in the invention."

And insert in its place the following:
--This invention was made with government support under NS039559 awarded by the National Institutes of Health. The government has certain rights in the invention.--

Signed and Sealed this
Thirtieth Day of April, 2019

Andrei Iancu
*Director of the United States Patent and Trademark Office*